US012582473B2

(12) United States Patent
Hutchens et al.

(10) Patent No.: US 12,582,473 B2
(45) Date of Patent: Mar. 24, 2026

(54) METHODS FOR SURFACTANT ENHANCED LASER-INDUCED VAPOR BUBBLES FOR USE IN LASER LITHOTRIPSY

(71) Applicant: The University of North Carolina at Charlotte, Charlotte, NC (US)

(72) Inventors: Thomas C. Hutchens, Charlotte, NC (US); Nicholas C. Giglio, Waxhaw, NC (US); Nathaniel M. Fried, Concord, NC (US)

(73) Assignee: The University of North Carolina at Charlotte, Charlotte, NC (US)

( * ) Notice: Subject to any disclaimer, the term of this patent is extended or adjusted under 35 U.S.C. 154(b) by 495 days.

(21) Appl. No.: 17/922,148

(22) PCT Filed: Apr. 29, 2021

(86) PCT No.: PCT/US2021/029902
§ 371 (c)(1),
(2) Date: Oct. 28, 2022

(87) PCT Pub. No.: WO2021/222572
PCT Pub. Date: Nov. 4, 2021

(65) Prior Publication Data
US 2023/0190373 A1 Jun. 22, 2023

Related U.S. Application Data

(60) Provisional application No. 63/017,212, filed on Apr. 29, 2020.

(51) Int. Cl.
A61B 18/26 (2006.01)
A61B 1/307 (2006.01)
A61B 18/00 (2006.01)

(52) U.S. Cl.
CPC .............. *A61B 18/26* (2013.01); *A61B 1/307* (2013.01); *A61B 2018/00511* (2013.01);
(Continued)

(58) Field of Classification Search
None
See application file for complete search history.

(56) References Cited

U.S. PATENT DOCUMENTS 4,127,413 A * 11/1978 Ishihara ............... G03C 7/3885
430/539
4,430,468 A * 2/1984 Schumacher ........ D06N 7/0076
524/427
(Continued)

FOREIGN PATENT DOCUMENTS

WO WO 2008/119945 A2 10/2008

OTHER PUBLICATIONS

JS Manne, The effect of polyanion, calcium and oxalate concentration on calcium oxalate crystallization and the effect of solution properties on the action of shock wave lithotripsy, Columbia University, ProQuest Dissertations & Theses, 9221184, 1992. (Year: 1992).*
(Continued)

*Primary Examiner* — Carl H Layno
*Assistant Examiner* — Manolis Pahakis
(74) *Attorney, Agent, or Firm* — Jenkins, Taylor & Hunt, P.A.

(57) ABSTRACT
Methods for surfactant enhanced laser-induced vapor bubbles for use in laser lithotripsy. Urinary tract stone disease is a common and costly disease that effects approximately 10% of the United States population. A preferred minimally invasive method for treatment of urinary tract stones is laser lithotripsy, which involves insertion of a flexible ureteroscope through the urinary tract to the stone's
(Continued)

108 t=0 μs 108    124 t=175 μs location, and then transmission of infrared (IR) laser energy through a flexible optical fiber, which is in turn placed through the single working channel of the ureteroscope. The IR laser energy is used for ablation of the urinary tract stone which is then removed. In order to have a more efficient ablation, the ureteroscope is fed with a surfactant composition which is flowed into the ureter and/or kidney of the subject. The laser causes larger bubbles to form in the surfactant composition, making a robust and longer lasting bubble.

16 Claims, 13 Drawing Sheets

(52) U.S. Cl.
CPC ............... *A61B 2018/00517* (2013.01); *A61B 2018/00577* (2013.01); *A61B 2018/263* (2013.01)

(56) References Cited

U.S. PATENT DOCUMENTS

| | | | | | |
|---|---|---|---|---|---|
| 5,092,864 | A | * | 3/1992 | Hayes | A61B 18/20 |
| | | | | | 606/16 |
| 5,321,715 | A | | 6/1994 | Trost | |
| 5,472,406 | A | * | 12/1995 | de la Torre | A61B 17/22022 |
| | | | | | 606/14 |
| 5,726,154 | A | * | 3/1998 | Baudys | A61K 38/23 |
| | | | | | 514/11.9 |
| 5,836,940 | A | * | 11/1998 | Gregory | A61B 18/245 |
| | | | | | 604/20 |
| 9,907,616 | B1 | | 3/2018 | Fried et al. | |

| | | | | |
|---|---|---|---|---|
| 2002/0120237 | A1 * | 8/2002 | Sahatjian | A61L 26/008 |
| | | | | 604/180 |
| 2005/0143678 | A1 * | 6/2005 | Schwarz | A61B 17/12099 |
| | | | | 601/4 |
| 2006/0229659 | A1 * | 10/2006 | Gifford | A61B 17/221 |
| | | | | 606/200 |
| 2010/0137847 | A1 * | 6/2010 | Cecchetti | A61B 18/26 |
| | | | | 606/2.5 |
| 2015/0344834 | A1 | 12/2015 | Mitragotri et al. | |
| 2016/0184022 | A1 * | 6/2016 | Grace | A61B 18/26 |
| | | | | 606/2.5 |
| 2016/0184023 | A1 | 6/2016 | Grace et al. | |
| 2017/0014446 | A1 | 1/2017 | Rolke et al. | |
| 2021/0153939 | A1 * | 5/2021 | Cook | A61B 18/26 |
| 2022/0313894 | A1 * | 10/2022 | Peled | A61B 18/26 |
| 2025/0169871 | A1 * | 5/2025 | Schultheis | A61B 18/245 |

OTHER PUBLICATIONS

Giglio et al., "Surfactant Enhanced Laser-Induced Vapor Bubbles for Potential Use in Thulium Fiber Lase Lithotripsy", 42nd Annual International Conference of the IEEE Engineering in Medicine & Biology Society, ppg. 5045-5048 (Aug. 27, 2020).
International Search Report and the Written Opinion of the International Searching Authority Corresponding to International Application No. PCT/US 2021/29902 dated Oct. 6, 2021.
N. M. Fried, "Recent advances in infrared laser lithotripsy," Biomed. Opt. Express, vol. 9, No. 9, pp. 4552-4568, 2018.
Y. A. Pishchalnikov, W. Behnke-Parks, K. Maeda, T. Colonius, M. Mellema, M. Hopcroft, A. Luong, S. Wiener, M. L. Stoller, and D. J. Laser, "Experimental observations and numerical modeling of lipid-shell microbubbles with calcium-adhering moieties for minimally-invasive treatment of urinary stones," Proc. Mtgs. Acoust., vol. 35, 020008, pp. 1-12, 2018.

* cited by examiner

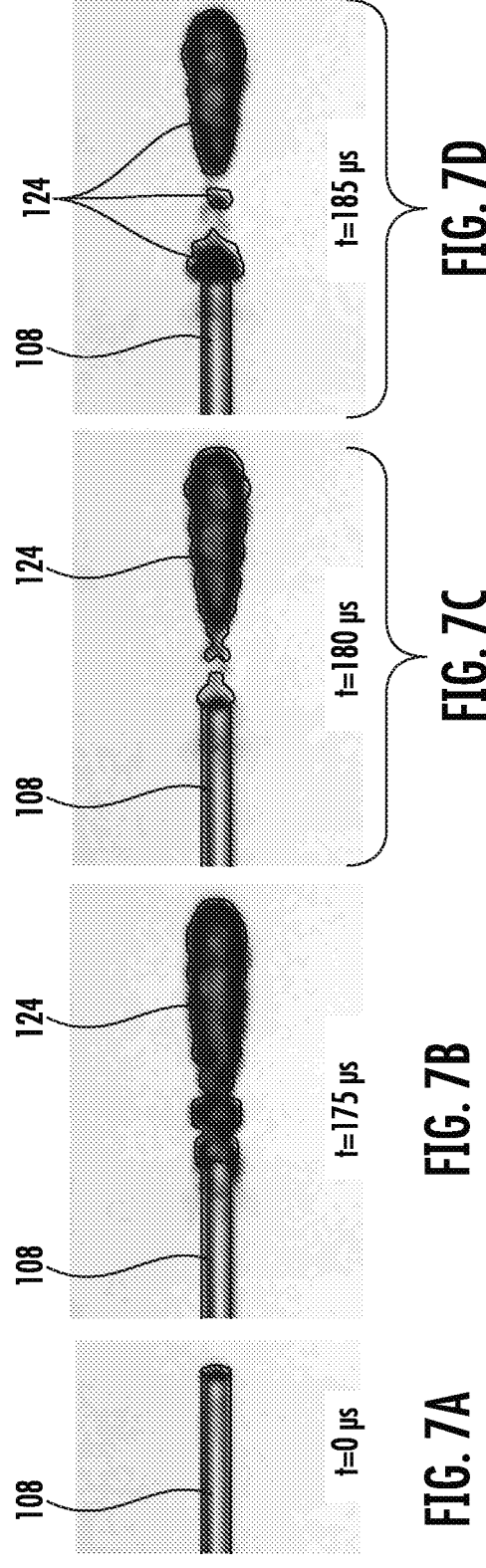

1100

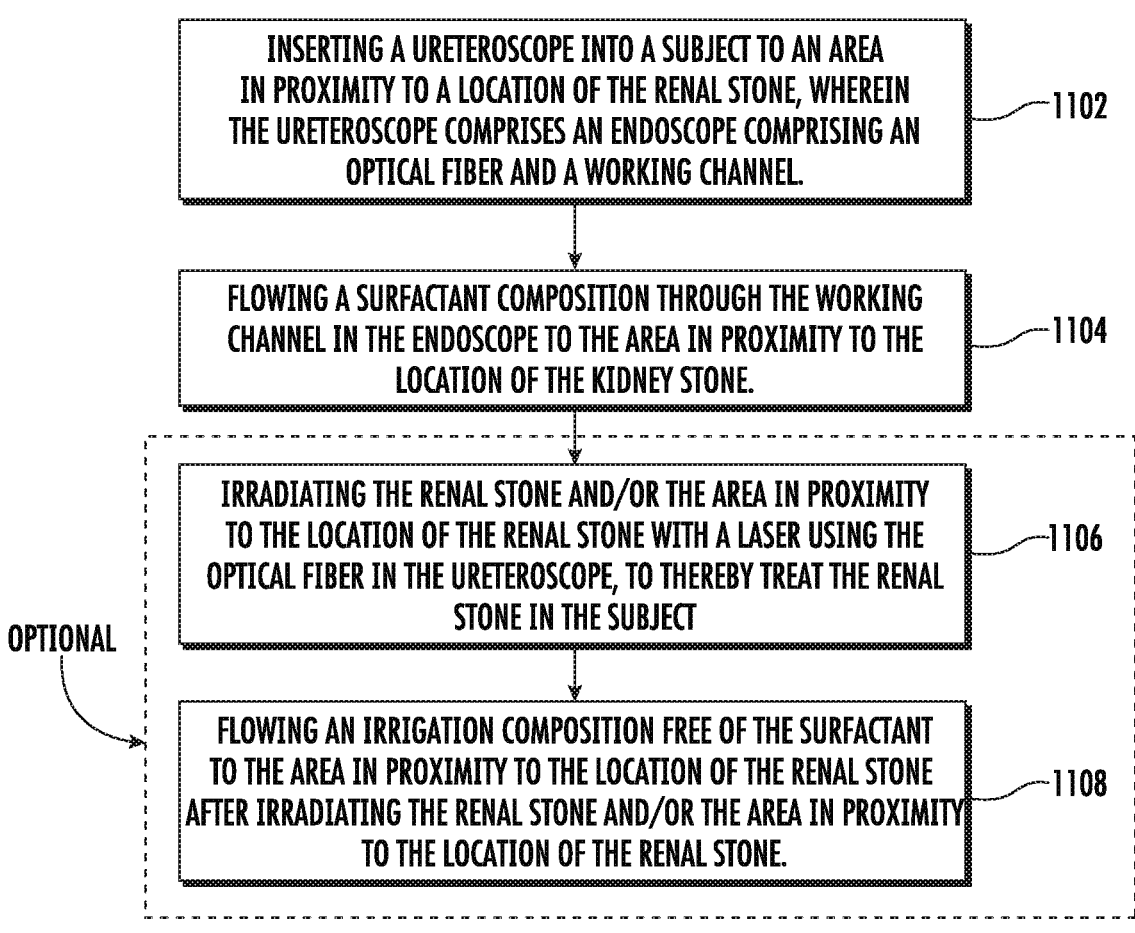

INSERTING A URETEROSCOPE INTO A SUBJECT TO AN AREA IN PROXIMITY TO A LOCATION OF THE RENAL STONE, WHEREIN THE URETEROSCOPE COMPRISES AN ENDOSCOPE COMPRISING AN OPTICAL FIBER AND A WORKING CHANNEL. — 1102

FLOWING A SURFACTANT COMPOSITION THROUGH THE WORKING CHANNEL IN THE ENDOSCOPE TO THE AREA IN PROXIMITY TO THE LOCATION OF THE KIDNEY STONE. — 1104

IRRADIATING THE RENAL STONE AND/OR THE AREA IN PROXIMITY TO THE LOCATION OF THE RENAL STONE WITH A LASER USING THE OPTICAL FIBER IN THE URETEROSCOPE, TO THEREBY TREAT THE RENAL STONE IN THE SUBJECT — 1106

OPTIONAL

FLOWING AN IRRIGATION COMPOSITION FREE OF THE SURFACTANT TO THE AREA IN PROXIMITY TO THE LOCATION OF THE RENAL STONE AFTER IRRADIATING THE RENAL STONE AND/OR THE AREA IN PROXIMITY TO THE LOCATION OF THE RENAL STONE. — 1108

FIG. 11

METHODS FOR SURFACTANT ENHANCED LASER-INDUCED VAPOR BUBBLES FOR USE IN LASER LITHOTRIPSY

CROSS-REFERENCE TO RELATED APPLICATIONS

The present application is a national stage filing of PCT International Application No. PCT/US2021/029902, filed Apr. 29, 2021, incorporated herein by reference in its entirety, and which claims the benefit of U.S. Provisional Patent Application Ser. No. 63/017,212, filed Apr. 29, 2020, the disclosure of which is incorporated by reference in its entirety.

TECHNICAL FIELD

The subject matter disclosed herein relates generally to laser lithotripsy. More particularly, the subject matter disclosed herein relates to surfactant enhanced laser-induced vapor bubbles for use in laser lithotripsy.

BACKGROUND

Kidney stone disease is a common and costly disease that effects approximately 10% of the United States population [1]. A preferred minimally invasive method for treatment of kidney stones is laser lithotripsy, which involves insertion of a flexible ureteroscope through the urinary tract to the stone's location, and then transmission of infrared (IR) laser energy through a flexible optical fiber, which is in turn placed through the single working channel of the ureteroscope.

For over 20 years, the Holmium:YAG laser with an IR wavelength of 2120 nm, has been the gold standard laser for lithotripsy, due in part to its ability to successfully fragment a variety of stone compositions, its relatively safe record for use in endourology, and availability of robust silica optical fibers for delivery of the laser energy through the urinary tract [2].

Recently, the Thulium fiber laser (TFL), with an IR wavelength of 1940 nm, has been introduced as a potential alternative to the Holmium:YAG laser for use in lithotripsy [3-7]. The TFL has several potential advantages, including: (1) an IR laser wavelength that is more strongly absorbed by water yielding a 4 times lower stone ablation threshold, (2) use with smaller optical fibers which are inherently more flexible and consume less cross-sectional area within the single working channel of the ureteroscope for enhanced saline irrigation rates and improved visibility and safety, and (3) a smaller, more compact, quieter, air-cooled, high-power laser system operated from a standard 110-volt outlet.

When IR lasers (e.g. Holmium and TFL) deliver energy through an optical fiber into a fluid environment (in this case, the urinary tract filled with fluid, augmented by the constant saline irrigation through the working channel of the ureteroscope during the lithotripsy procedure), a vapor bubble is created at the distal or delivery fiber optic tip. This laser-induced vapor bubble results from the strong water absorption at these specific IR laser wavelengths. For the application of laser lithotripsy, the vapor bubble produces both advantageous and disadvantageous effects. First, the vapor bubble displaces the highly absorbing fluid, thus enabling a channel for laser lithotripsy to be conducted in a non-contact mode with the fiber tip to stone distance in close proximity (on the order of a few millimeters). Second, the rapid expansion and contraction of the vapor bubble may produce significant pressure transients capable of removing stone material and providing a mechanical contribution to ablation [3,4,8], which augments the otherwise primarily photothermal mechanism associated with long-pulse laser lithotripsy [9,10]. However, these pressure transients may also contribute to the undesirable phenomenon of stone "retropulsion" in which the stone is propelled backwards, away from the fiber tip, thus requiring the urologist to waste valuable operating room time and "chase after a moving target in the urinary tract." Thus, approaches that can be implemented to improve laser lithotripsy procedures represent an ongoing need in the art.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides a method of irradiating a target with laser radiation. In some embodiments, the radiation is delivered to the target by an optical fiber having a delivery end.

In some embodiments, the delivery end is spaced from the target. In some embodiments, the space between the delivery end of the optical fiber and the target is occupied with a liquid medium. In some embodiments, the laser radiation has a wavelength which is absorbed in the liquid medium. In some embodiments, the method comprises (a) administering a surfactant composition to the liquid medium; (b) generating a first laser pulse having sufficient energy to form a vapor bubble in the liquid medium at the delivery end of the optical fiber; and (c) allowing the vapor bubble to expand an amount sufficient to displace a portion of the liquid medium from the space between the delivery end of the optical fiber and the target. In some embodiments, the method further comprises generating one or more additional laser pulses, the one or more additional laser pulses being delivered to the target through the vapor bubble.

In some embodiments, the target is located in an area internal to a subject and the liquid medium is present in the area internal to the subject. In some embodiments, the target is a tissue or other structure in the subject. In some embodiments, the other structure is a urinary tract stone, a gastrointestinal stone, or a salivary stone.

In some embodiments, the presently disclosed subject matter provides a method of delivering a surfactant composition to a subject. In some embodiments, the method comprises: (a) inserting an endoscope into a subject to an area internal to the subject where delivery of a surfactant composition is desired, wherein the endoscope comprising an optical fiber and a working channel; and (b) flowing a surfactant composition through the working channel in the endoscope to the area in the subject. In some embodiments, the area in the subject comprises a target to be treated by laser radiation. In some embodiments, the target to be treated in the subject is a tissue in the subject, or is the subject is suffering from a urinary tract stone, a gastrointestinal stone, or a salivary stone in the subject. In some embodiments, the area in the subject is in proximity to the location of the target and wherein the area comprises a liquid medium; and the method further comprises irradiating the stone target and/or the area in proximity to the location of the target with a laser using the optical fiber in the endoscope, to thereby treat the target in the subject, wherein the laser is operated at a wavelength which is absorbed in the liquid medium. In some embodiments, the urinary tract stone is in the kidney, ureter, or bladder of the subject.

In some embodiments, the irradiating with the laser induces formation of a vapor bubble at a delivery tip of the optical fiber of the endoscope. In some embodiments, the method further comprises generating one or more additional laser pulses, the one or more additional laser pulses being delivered to the target through the vapor bubble.

In some embodiments, the method further comprises flowing an irrigation composition free of the surfactant to the area in proximity to the location of the target after irradiating the target and/or the area in proximity to the location of the target. In some embodiments, the irradiating with the laser generates one or more fragments of the target and the method comprises collecting the one or more fragments.

In some embodiments, a system for carrying delivering a surfactant composition to a target is provided. In some embodiments, the target is in the body of a subject. In some embodiments, the system comprises: (a) an endoscope comprising a flexible outer sheath, a working channel within the outer sheath, and a flexible optical fiber passing within the outer sheath, the flexible optical fiber configured to couple with a light source; and (b) a reservoir comprising a surfactant composition, wherein the reservoir and the working channel of the endoscope are configured for fluidic connection with each other. In some embodiments, the endoscope and reservoir are configured for carrying a surfactant composition into the body of a subject. In some embodiments, the endoscope and reservoir are configured for implementation in laser lithotripsy and the system comprises instructions for implementing the system in laser lithotripsy.

In some embodiments, the presently disclosed subject matter provides a laser lithotripsy system. In some embodiments, the laser lithotripsy system comprises: (a) a ureteroscope comprising an eyepiece at a first end of the ureteroscope and an endoscope extending away from the eyepiece to define a second end of the ureteroscope, wherein the second end is sufficiently spaced away from the first end so as to reach a kidney of a subject when the laser lithotripsy system is in use, and wherein the endoscope comprises a flexible outer sheath, a working channel within the outer sheath, and a flexible optical fiber passing within the outer sheath; (b) a reservoir comprising a surfactant composition, wherein the reservoir and the working channel of the endoscope are configured for fluidic connection with each other; (c) a laser light source, wherein the laser light source and the flexible optical fiber are configured for operable connection with each other; and (d) a control system configured for operable connection with the ureteroscope, the reservoir, and/or the laser light source. In some embodiments, the system comprises a basket for collecting one or more fragments of a target, e.g, a stone, the basket controllably disposed in the working channel of the endoscope.

In some embodiments, the system comprises a detection system for observing an environment in which the endoscope is implemented and/or an illumination system for illuminating an environment in which the endoscope is implemented, wherein the detection system and illumination system are controlled by the control system.

In some embodiments, the system comprises a reservoir comprising an irrigation composition free of the surfactant, wherein the reservoir and the working channel are configured for fluidic connection with each other. In some embodiments, the system comprises a line for connecting the reservoir comprising the surfactant composition and the working channel of the endoscope; and/or a line for connecting the reservoir containing the surfactant-free irrigation composition to the working channel of the endoscope. In some embodiments, the system comprises one or more valves configured for controlling flow from the line for connecting the reservoir comprising the surfactant composition to the working channel of the endoscope and from the line for connecting the reservoir containing the surfactant-free irrigation composition to the working channel of the endoscope. In some embodiments, the system comprises one or more manual pumps configured for controlling flow from the line for connecting the reservoir comprising the surfactant composition to the working channel of the endoscope and from the line for connecting the reservoir containing the surfactant-free irrigation composition to the working channel of the endoscope. In some embodiments, the one or more manual pumps comprises one or more syringes.

In some embodiments, the laser is operated at an infrared wavelength, optionally wherein a wavelength of the laser ranges from about 1450 nm to about 2200 nm. In some embodiments, the laser is selected from the group comprising an indium phosphide diode laser, a thulium fiber laser (TFL), a thulium:YAG solid-state laser, and a holmium: YAG solid-state laser.

In some embodiments, the laser is operated at one or more parameters selected from the group comprising: (a) a pulse energy ranging from about 0.025 to about 6.0 Joules; (b) a pulse duration ranging from about 200 to about 20,000 microseconds; (c) a pulse repetition rate ranging from about 5 to about 2,000 Hertz; and (d) an average power ranging from about 1 to about 200 watts.

In some embodiments, the presently disclosed subject matter provides a kit. In some embodiments, the kit comprises a reservoir comprising a surfactant composition; and instructions for implementing the reservoir in a system for delivering the surfactant composition to a target. In some embodiments, the reservoir is configured for implementation in a laser lithotripsy system and the instructions are for implementing the reservoir in a laser lithotripsy system. In some embodiments, the kit comprises a reservoir comprising an irrigation composition free of the surfactant. In some embodiments, the kit comprises a line for connecting the reservoir comprising the surfactant composition to a working channel of an endoscope; and/or a line for connecting the reservoir containing the surfactant-free irrigation composition to a working channel of an endoscope. In some embodiments, the kit comprises one or more valves configured for controlling flow from the line for connecting the reservoir comprising the surfactant composition to the working channel of the endoscope and from the line for connecting the reservoir containing the surfactant-free irrigation composition to the working channel of the endoscope.

In any of the above-described embodiments, the surfactant composition can comprise (a) a surfactant at a concentration of about 0.1% to about 10% by weight of total composition; and (b) a carrier suitable for administration in a liquid medium in the area in the subject. In some embodiments, the surfactant is present at a concentration ranging from about 1% to about 2% by weight of total composition. In some embodiments, the surfactant is selected from the group consisting of an anionic surfactant, a nonionic surfactant, a cationic surfactant, and a zwitterionic surfactant. In some embodiments, the nonionic surfactant is a polysorbate surfactant. In some embodiments, the polysorbate surfactant is selected from the group consisting of polysorbate 20, polysorbate 60, and polysorbate 80. In some embodiments, the carrier comprises a component selected from the group comprising water, a buffer, an electrolyte, a solution suitable for intravenous administration in a subject, and a solution isotonic to the liquid medium. In some embodiments, the electrolyte is selected from the group comprising sodium, chlorine, potassium, and combinations thereof. In some embodiments, the electrolyte is present as sodium chloride at a concentration of about 0.3% to about 1.2% by weight of total solution.

In any of the above-described embodiments, an outer shell of the reservoir is made from medical grade plastic.

In some embodiments, a surfactant composition is provided. In some embodiments, the surfactant composition is adapted for implementation in a liquid medium comprising a target for a laser. In some embodiments, the composition comprises (a) a surfactant at a concentration of about 0.1% to about 10% by weight of total composition; and (b) a carrier suitable for administration in a liquid medium. In some embodiments, the surfactant is present at a concentration ranging from about 1% to about 2% by weight of total composition. In some embodiments, the surfactant is selected from the group consisting of an anionic surfactant, a nonionic surfactant, a cationic surfactant, and a zwitterionic surfactant. In some embodiments, the nonionic surfactant is a polysorbate surfactant. In some embodiments, the polysorbate surfactant is selected from the group consisting of polysorbate 20, polysorbate 60, and polysorbate 80. In some embodiments, the carrier comprises a component selected from the group comprising water, a buffer, an electrolyte, a solution suitable for intravenous administration in a subject, and a solution isotonic to the liquid medium. In some embodiments, the electrolyte is selected from the group comprising sodium, chlorine, potassium, and combinations thereof. In some embodiments, the electrolyte is present as sodium chloride at a concentration of about 0.3% to about 1.2% by weight of total solution. In some embodiments, the composition is adapted for implementation in a laser lithotripsy system.

In some embodiments, a Thulium fiber laser (TFL) is used as an alternative to the gold standard Holmium: YAG laser for ablation of kidney stones. Infrared laser-induced vapor bubbles contribute to both the ablation mechanism and stone retropulsion. In some embodiments, a biocompatible surfactant with concentrations of 1-5% was used to enhance the vapor bubble dimensions during the laser pulse. Bubble dimensions using surfactant increased on average by 25% compared with water only (control). In further embodiments, introduction of the surfactant into the saline irrigation flow typically delivered through the working channel of the ureteroscope during laser lithotripsy, contributes to more efficient stone ablation.

Accordingly, it is an object of the presently disclosed subject matter to provide delivery of a surfactant composition to a target, such as a target in the body of a subject, such as for use in laser lithotripsy. An object of the presently disclosed subject matter having been stated hereinabove, and which is achieved in whole or in part by the presently disclosed subject matter, other objects will become evident as the description proceeds when taken in connection with the accompanying figures as best described hereinbelow.

BRIEF DESCRIPTION OF THE FIGURES

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which

FIG. 7A through FIG. 7D includes camera frames showing stages of vapor bubble formations;

FIG. 11 illustrates a flow chart detailing an example laser lithotripsy method according to some embodiments of the present disclosure.

DETAILED DESCRIPTION

Figure 1:
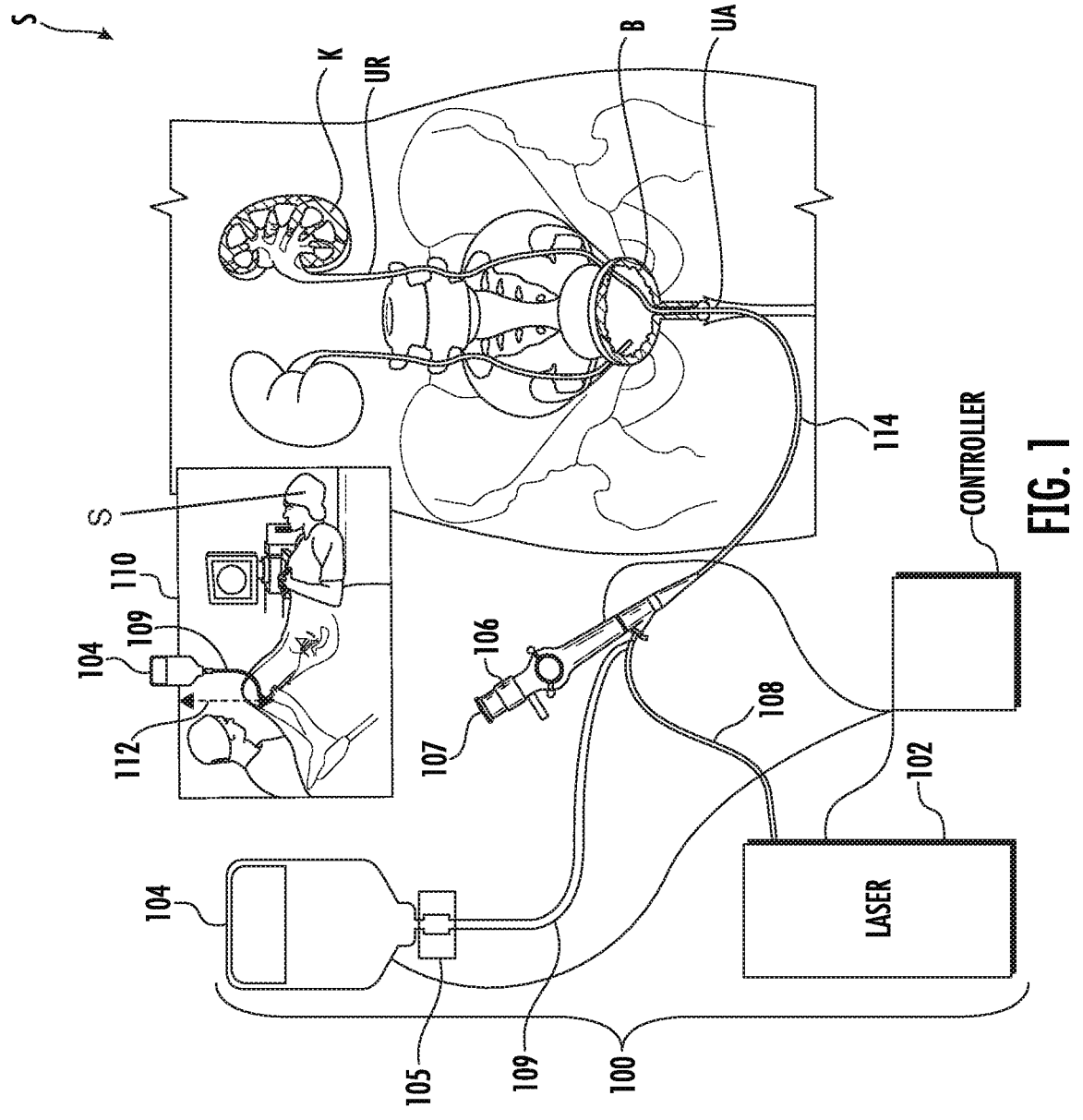
FIG. 1 illustrates an example laser lithotripsy system according to some embodiments of the present disclosure.

The disclosure hereinbelow provides systems and methods for delivery of a surfactant composition to an area in a subject's body comprising a target for treatment, for example, to treat a target tissue, and/or to treat one or more urinary tract stone, renal stones, bladder stones, and/or ureter stones in a subject using a laser lithotripsy system. Kidney stone disease is a common and costly disease that effects approximately 10% of the United States population [1]. A preferred minimally invasive method for treatment of kidney stones is laser lithotripsy, which involves insertion of a flexible ureteroscope through the urinary tract to the stone's location, and then transmission of infrared (IR) laser energy through a flexible optical fiber, which is in turn placed through the single working channel of the ureteroscope. For over 20 years, the Holmium:YAG laser with an IR wavelength of 2120 nm, has been the gold standard laser for lithotripsy, due in part to its ability to successfully fragment a variety of stone compositions, its relatively safe record for use in endourology, and availability of robust silica optical fibers for delivery of the laser energy through the urinary tract [2]. Recently, the Thulium fiber laser (TFL), with an IR wavelength of 1940 nm, has been introduced as a potential alternative to the Holmium:YAG laser for use in lithotripsy [3-7]. The TFL has several potential advantages, including: (1) an IR laser wavelength that is more strongly absorbed by water yielding a 4 times lower stone ablation threshold, (2) use with smaller optical fibers which are inherently more flexible and consume less cross-sectional area within the single working channel of the ureteroscope for enhanced saline irrigation rates and improved visibility and safety, and (3) a smaller, more compact, quieter, air-cooled, high-power laser system operated from a standard 110-volt outlet.

In some embodiments, the presently disclosed subject matter evaluates whether a surfactant can be mixed with the normal saline (0.9% NaCl by weight in water (9 g/1 L)) irrigation typically delivered through the working channel of the ureteroscope, to artificially enhance the TFL induced vapor bubbles. Two representative, non-limiting aspects were evaluated. First, the lower laser energy required to produce the vapor bubble provides a more efficient lithotripsy procedure. Second, in the clinic, a "popcorn" method is commonly used in the difficult-to-reach calyces of the kidney, when removal of stone fragments using a stone extraction basket is not feasible. In this case, the laser energy is intentionally delivered into the saline medium, resulting in turbulent flow, and movement of the stones in close proximity with the fiber optic tip for ablation. Enhanced laser-induced vapor bubble dimensions makes this popcorn ablation method more efficient as well.

In some embodiments, the presently disclosed subject matter provides a method of irradiating a target with laser radiation. In some embodiments, the radiation is delivered to the target by an optical fiber having a delivery end.

In some embodiments, the delivery end is spaced from the target. In some embodiments, the space between the delivery end of the optical fiber and the target is occupied with a liquid medium. In some embodiments, the laser radiation has a wavelength which is absorbed in the liquid medium. In some embodiments, the method comprises (a) administering a surfactant composition to the liquid medium; (b) generating a first laser pulse having sufficient energy to form a vapor bubble in the liquid medium at the delivery end of the optical fiber; and (c) allowing the vapor bubble to expand an amount sufficient to displace a portion of the liquid medium from the space between the delivery end of the optical fiber and the target. In some embodiments, the method further comprises generating one or more additional laser pulses, the one or more additional laser pulses being delivered to the target through the vapor bubble.

In some embodiments, the target is located in an area internal to a subject and the liquid medium is present in the area internal to the subject. In some embodiments, the target is a tissue or other structure in the subject. In some embodiments, the other structure is a urinary tract stone, a gastro-intestinal stone, or a salivary stone.

While the following terms are believed to be well understood by one having ordinary skill in the art, the following definitions are set forth to facilitate explanation of the presently disclosed subject matter.

Unless defined otherwise, all technical and scientific terms used herein have the same meaning as commonly understood to one having ordinary skill in the art to which the presently disclosed subject matter belongs. Although, any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a heat exchanger" can include a plurality of such heat exchangers, and so forth.

Unless otherwise indicated, all numbers expressing quantities of length, diameter, width, and so forth used in the specification and claims are to be understood as being modified in all instances by the terms "about" or "approximately". Accordingly, unless indicated to the contrary, the numerical parameters set forth in this specification and attached claims are approximations that can vary depending upon the desired properties sought to be obtained by the presently disclosed subject matter.

As used herein, the terms "about" and "approximately," when referring to a value or to a length, width, diameter, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate for the disclosed apparatuses and devices.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and sub-combinations of A, B, C, and D.

FIG. 1 illustrates an example laser lithotripsy system 100 configured for aiding a medical professional or other user in finding and treating one or more stones of the urinary tract, e.g., kidney (renal) stones, ureter stones, and/or bladder stones, from a subject S. In some embodiments, the system 100 comprises a ureteroscope 106, one or more containers or reservoirs 104 comprising a surfactant composition, the reservoir 104 being configured for fluidic connection with the ureteroscope 106, a laser light source or a laser 102 operably connected to the ureteroscope 106 via a flexible optical fiber 108, and an endoscope 114 operably connected to the ureteroscope 106.

In some embodiments, the laser light source or laser 102, reservoir 104, and ureteroscope 106 can all be connected to and controlled by a control system or controller C. In some embodiments, the control system or controller C can comprise one or more processors or other circuitry configured to operate and control the various functions of the system 100. In some embodiments, the controller C can be connected to a display, screen, monitor, or other display device configured to display one or more pictures or video(s) captured by one or more camera of the ureteroscope 106.

In some embodiments, the laser 102 comprises an indium phosphide diode laser, a thulium fiber laser (TFL), a thulium:YAG solid-state laser, or a holmium:YAG solid-state laser. In some embodiments, the laser 102 is configured to generate a laser having a wavelength in the infrared portion of the electromagnetic spectrum. More particularly, in some embodiments, the laser 102 can be configured to generate a laser having a wavelength of between, and including, about 1450 nm to about 2200 nm. For example and without limitation, the laser 102 can be configured to generate a laser having a wavelength of about 1470 nm, a wavelength between, and including, about 1908 nm and 1940 nm, a wavelength of about 2010 nm, or 2120 nm. In any embodiment where the laser 102 is included, the laser 102 comprises a flexible optical fiber 108 which operably connects to the ureteroscope 106 and is carried by the endoscope 114 to be inserted into the urethra U of the subject S. The length of the flexible optical fiber 108 can be greater than the length of the endoscope 114 such that the flexible optical fiber 108 can be carried through the body of the subject S within the endoscope 114 and exit the tip of the endoscope 114 for the laser light to enter the body of the subject S for treatment. In some embodiments, the laser 102 is configured to generate laser radiation at a wavelength such that the laser radiation is absorbed in the liquid medium present in the area internal to the subject.

In some embodiments, the laser 102 is operated at a pulse energy ranging between, and including, about 0.025 and 6 Joules. For example and without limitation, the laser 102 is operated at a pulse energy of about 0.025, 0.05, 0.1, 0.15, 0.2, 0.4, 0.5, 0.8, 1.0, 1.5, 2, 3, 4, 5, or 6 Joules. In some embodiments, the laser 102 is operated at a pulse duration ranging between, and including, about 200 to 20,000 microseconds. In some embodiments, for example and without limitation, the laser 102 is operated at a pulse duration of about 200, 250, 400, 500, 800, 1000, 1500, 2500, 3000, 6000, 10,000, 12,000, 15,000, or 20,000 microseconds. In some embodiments, the laser 102 is operated at a pulse repetition rate ranging between, and including, about 5 and 2,000 Hertz. In some embodiments, for example and without limitation, the laser is operated at a pulse repetition rate of about 5, 10, 20, 40, 80 120, 240, 480, 500, 1000, 1500, or 2000 Hertz. In some embodiments, the laser 102 is operated at an average power ranging between, and including, about 1 and 200 watts. In some embodiments, for example and without limitation, the laser 102 is operated at an average power of about 1, 2, 5, 10, 20, 40, 60, 80, 100, 120, 140, 160, 180, or 200 watts.

In some embodiments, a first laser pulse is generated, having sufficient energy to form a vapor bubble in the liquid medium at the delivery end of the optical fiber; and allowing the vapor bubble to expand an amount sufficient to displace a portion of the liquid medium from the space between the delivery end of the optical fiber and the target. In some embodiments, the method further comprises generating one or more additional laser pulses, the one or more additional laser pulses being delivered to the target through the vapor bubble.

In some embodiments, the reservoir 104 can be an IV bag, one or more IV bags, or any other suitable reservoir or container that can contain the irrigation fluid as described herein. In other words, while one IV bag is shown in FIG. 1 multiple IV bags could be included with a valve to switching between the bags. In some embodiments, an outer shell of the reservoir is made from medical grade plastic.

In some embodiments, the reservoir 104 comprises an irrigation fluid (e.g. solution or suspension) comprising a surfactant composition and one or more other fluids or a carrier suitable for administration in laser lithotripsy system like that described herein, in an irrigation mixture (e.g., solution or suspension). The compositions of the presently disclosed subject matter comprise, in some embodiments, a composition that includes a pharmaceutically acceptable carrier. Any suitable pharmaceutical formulation can be used to prepare the compositions for administration to a subject. In some embodiments, the composition and/or carriers can be pharmaceutically acceptable in humans.

For example, suitable formulations can include aqueous and non-aqueous sterile intravenous solutions that can contain anti-oxidants, buffers, bacteriostatics, bactericidal antibiotics, and solutes that render the formulation isotonic with the bodily fluids of the subject; and aqueous and non-aqueous sterile suspensions that can include suspending agents and thickening agents. The surfactant can be provided, such as in a kit as described herein below, in the reservoir or other container in powder or other dry form, requiring only the addition of a liquid carrier, such as a sterile liquid carrier, for example water for administration into the body of a subject, immediately prior to use.

It should be understood that in addition to the ingredients particularly mentioned above, the formulations of the presently disclosed subject matter can include other agents conventional in the art having regard to the type of formulation in question. For example, sterile pyrogen-free aqueous and non-aqueous solutions can be used.

By way of additional example and without limitation, the additional fluids or carrier can comprise saline, sterile water, lactated Ringer's, sodium chloride and water, or at least one electrolyte and water, or any other suitable fluid. In some other embodiments, the carrier can comprise a substance suitable as a viscosity modifier. In some embodiments, the irrigation fluid in the reservoir 104 can comprise a mixture of fluids, including the surfactant composition, wherein the surfactant concentration in the irrigation fluid is between, and including, about 0.1% and 10% by weight. In some embodiments, a surfactant composition is provided. In some embodiments, the surfactant composition is adapted for implementation in a liquid medium comprising a target for a laser.

In some embodiments, the composition comprises (a) a surfactant at a concentration of about 0.1% to about 10% by weight of total composition; and (b) a carrier suitable for administration in a liquid medium. In some embodiments, the surfactant is present at a concentration ranging from about 0.1%, 0.5%, 1%, 2%, 3%, 4%, 5%, 6%, 7%, 8%, 9%, or 10% by weight of total composition. In some embodiments, the surfactant is selected from the group comprising an anionic surfactant, a nonionic surfactant, a cationic surfactant, and a zwitterionic surfactant. In some embodiments, the nonionic surfactant is a polysorbate surfactant. In some embodiments, the polysorbate surfactant is selected from the group comprising polysorbate 20 (available under the registered trademark Tween® 20), polysorbate 60 (available under the registered trademark Tween® 60), and polysorbate 80 (available under the registered trademark Tween® 80). In some embodiments, the carrier comprises a component selected from the group comprising water, a buffer, an electrolyte, a solution suitable for intravenous administration in a subject, and a solution isotonic to the liquid medium. In some embodiments, the electrolyte is selected from the group comprising sodium, chlorine, potassium, and combinations thereof. In some embodiments, the electrolyte is present as sodium chloride at a concentration of about 0.3% to about 1.2% by weight of total solution. In some embodiments, the composition is adapted for implementation in a laser lithotripsy system.In some embodiments, the surfactant comprises a sugar-based surfactant. Some exemplary surfactants include Arlacel-60® (sorbitan stearate), Arlacel-80® (sorbitan oleate), sodium dodecyl sulfate (SDS) and/or mannitol or another sugar. However, any suitable surfactant can be used based on its biocompatibility and potential for use in irrigation for laser lithotripsy. The type of surfactant to be used can also be based on the viscosity of the surfactant. Additionally, any suitable surfactant can be used that is biocompatible that effectively lowers surface tension of the laser-induced vapor bubbles in the liquid medium in the area of the target for the laser, thus increasing their physical dimensions (e.g., width and length) and duration.

As part of the system 100, the irrigation fluid in the reservoir 104 has multiple purposes, including delivering the surfactant and other fluid or carrier to the ureteroscope 106 via the connecting line 109 (i.e., IV tube or other suitable connecting line) and eventually the liquid arrives at the kidney K, including in the liquid medium present in the kidney, via the endoscope 114. The irrigation fluid and surfactant are then used to flush areas of the kidney K and/or help the laser 102 inflate one or more bubbles (i.e., bubbles comprising the surfactant composition) inside the kidney K near a kidney stone that needs treatment. That is, the target for treatment can be a stone, or other tissue. The usage of the bubble will be described in further detail hereinbelow. In some embodiments, in order to ensure that the irrigation fluid is delivered to the kidney K, the irrigation fluid can either be pumped or gravity fed to the subject S. For example and without limitation, in some embodiments, the system 100 can comprise an automatic or manual pump, valve 105, or other device attached to the reservoir 104 that is configured to automatically pump or push irrigation fluid to the subject S through the endoscope 114. In some other embodiments, the system 100 comprises a manual pump, such as, for example and without limitation, a syringe (i.e., instead of a reservoir like 104, the reservoir 104 can be replaced with a syringe) connected to the tubing that connects the reservoir 104 to the ureteroscope 106 and configured to provide a pumping pressure on the irrigation fluid towards the subject S via the endoscope 114. In yet another embodiment, the system 100 can use gravity to help cause the irrigation fluid to enter the subject S. As shown in the cut-out 110, the reservoir 104 can be positioned at a height 112 above the body of the subject S such that gravity will feed the irrigation fluid through the tubing and the endoscope 114 to the kidney K. In some embodiments, the height 112 of the reservoir 104 compared to the subject S is between, and including, about 0.3 to 1.0 m above the subject S. For example and without limitation, the height 112 of the reservoir 104 compared to the subject S can be about 0.3, 0.4, 0.5, 0.6 0.7, 0.8, 0.9, or 1 m above the subject S. Of note, during a laser lithotripsy procedure, the subject S or patient is under general anesthesia.

In some embodiments, the ureteroscope 106 comprises an eyepiece 107 at a first end and an endoscope 114 extending away from the eyepiece 107 to define a second end of the ureteroscope 106. The endoscope 114 is a long flexible tube configured to be inserted into the urethra UA of a subject S and eventually, the medical professional or other user of the ureteroscope 106 and endoscope 114 can feed the device up one of the ureters of the subject S and reach the kidney K. Those having ordinary skill in the art will appreciate that the endoscope 114 comprises at least a partially hollow tube having one or more separate channels that run the length of the body of the endoscope tube from the ureteroscope 106 to the end of the endoscope 114. As will be described further herein, the endoscope 114 is configured to carry both the tube for the irrigation fluid and the optical fiber 108 for the laser 102 within one or more of its channels. Alternatively, the tube for the reservoir 104 can connect to the endoscope 114 through the body of the ureteroscope 106 and the tube from the reservoir 104 can feed directly into one of the channels of the endoscope without the tube of the reservoir 104 running the whole length of the endoscope 114. These details will be further described hereinbelow. The endoscope 114 and reservoir 104 are configured for implementation in laser lithotripsy and the system comprises instructions for implementing the system 100 in laser lithotripsy.

In some embodiments, the eyepiece 107 of the ureteroscope 106 can be used to determine where the endoscope 114 is traveling in the body of the subject S as it is fed up the urethra UA, bladder B, ureter UR, and eventually, into the kidney K of the subject S. In alternative embodiments, video or pictures captured from a camera of the endoscope 114 or ureteroscope 106 can be transmitted to a screen, monitor, display, or other device for the medical professional or user to view and maneuver the endoscope 114.

Figure 2:
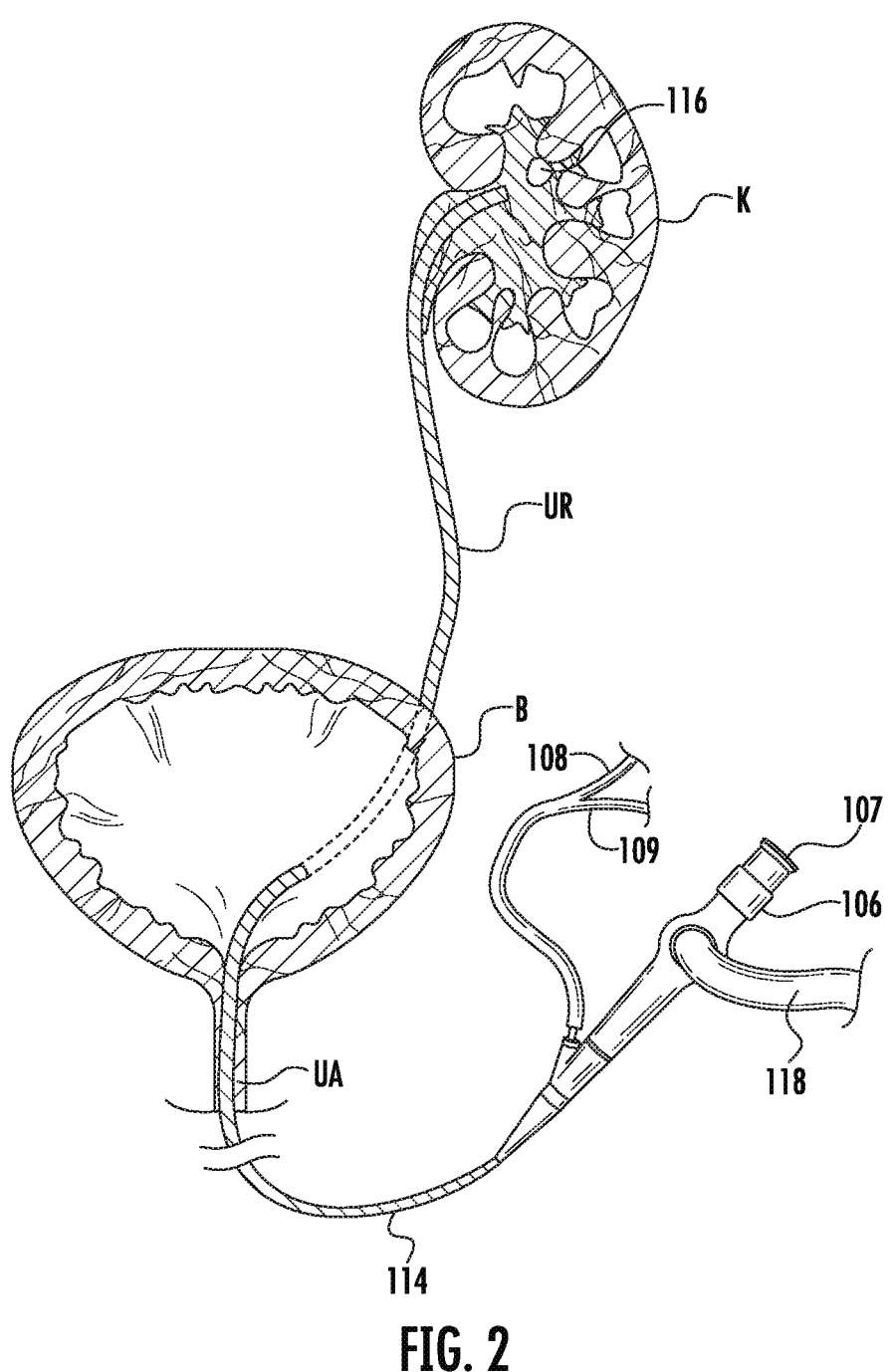
FIG. 2 illustrates an example laser lithotripsy system according to some embodiments of the present disclosure being used to perform kidney stone ablation and removal.

FIG. 2 illustrates a zoomed-in view of the ureteroscope 106 and the endoscope 114 being inserted into the urethra UA of the subject, then into the bladder B, through the ureter UR, and terminating at the kidney K near a urinary tract stone such as kidney stone 116. While some depictions herein illustrate a kidney stone 116, the stone could be any urinary tract stone such as, for example and without limitation, a kidney stone, a ureter stone, a bladder stone, etc. In order to provide power and control signals to the ureteroscope 106 as well as provide camera, video, and other data output to the monitor/display or other computer, processing unit, server, etc. from the ureteroscope 106, a power and data connection 118 can be provided to the ureteroscope 106. In some embodiments, the ureteroscope 106 and the endoscope 114 are flexible and steerable by the medical professional or user operating the ureteroscope 106. As shown in FIG. 2, the endoscope 114 is configured to be steered very close to the kidney stone 116 to be able to provide laser energy to the stone 116 for treatment. In some embodiments, the endoscope 114 comprises a flexible outer sheath, a working channel (described further hereinbelow) within the outer sheath, and a flexible optical fiber passing within the working channel.

Furthermore, the tube from the reservoir 104 and the optical fiber 108 can be fed together into the ureteroscope 106. At least the optical fiber 108 then goes into the endoscope 114 running the entire length of the endoscope 114 and terminates outside the end of the endoscope 114 that is in the kidney K. As described herein, the tube for the reservoir 104 can terminate at the ureteroscope 106 but the tube is fluidically connected to at least one of the channels that runs through the endoscope 114 to the end that is inserted into the kidney K in FIG. 2. In this configuration, the irrigation fluid from the reservoir 104 runs down the reservoir tube into the ureteroscope 106 and then makes its way into one of the channels of the endoscope 114, and finally flows through the endoscope 114 into the kidney K.

Figure 3A:
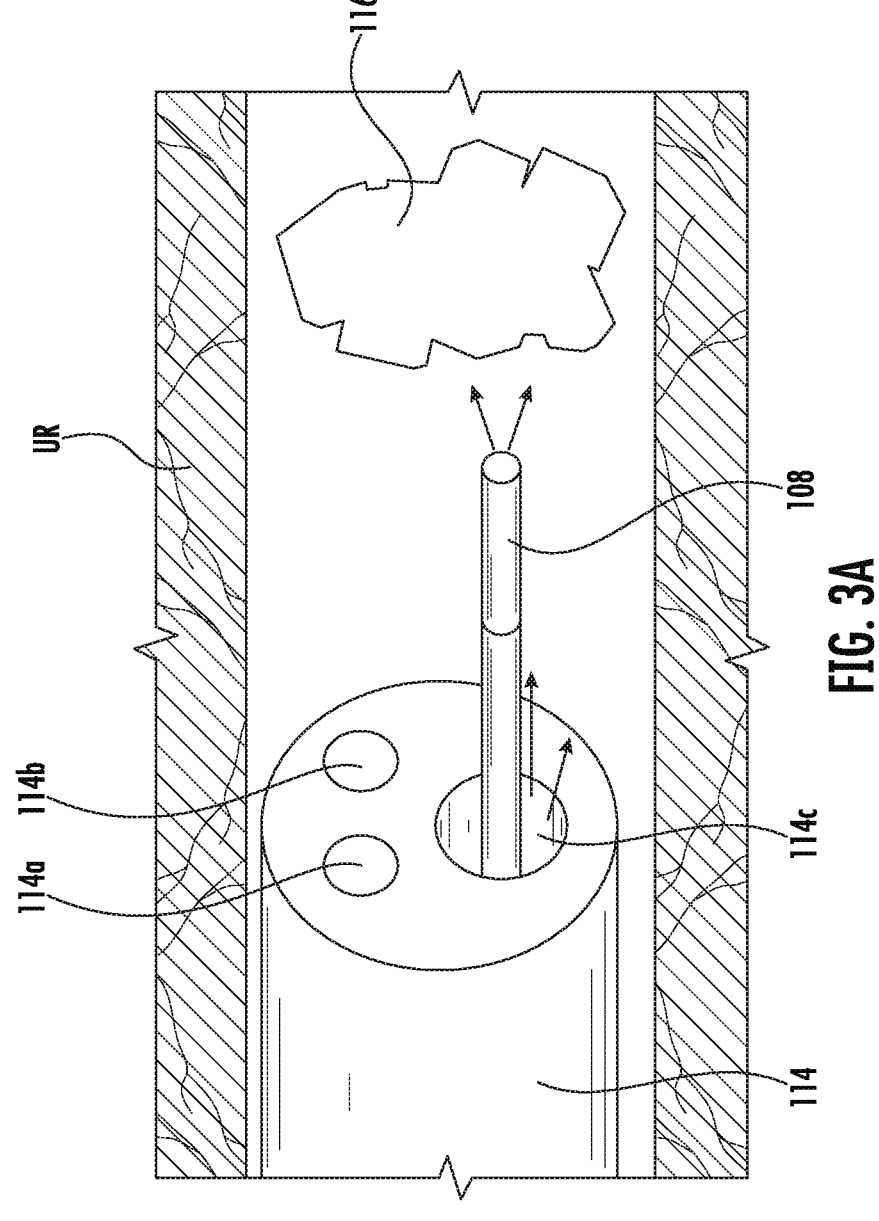
FIG. 3A and FIG. 3B illustrates a close-up view of the example laser lithotripsy system according to some embodiments of the present disclosure being used to perform kidney stone ablation and removal.

FIG. 3A is a zoomed-in illustration of the end of the endoscope 114 that is inserted into the subject's urinary tract next to a kidney stone 116 that is passing into the ureter UR of the subject. As described above, in some embodiments, the endoscope 114 can comprise one or more channels that run throughout its length. For example and without limitation, the endoscope can comprise a detection channel 114a which can comprise a camera capable of capturing videos or pictures in low-light or no-light environments. In some other embodiments, the detection channel 114a can comprise a camera that is capable of taking pictures or video with of objects that are illuminated. To that end, in some embodiments, the endoscope 114 can comprise an illumination channel 114b configured to carry am illumination or light source, such as, for example and without limitation, an LED light, a telescopic flashlight, a flashlight, or any other suitable lighting or illumination source.

In some embodiments, the camera and light source of the detection channel 114a and illumination channel 114b can be controlled by the control system described above. In such an embodiment, the control system can be configured with a touch screen or other actuator that allows the medical professional or other user to turn on and off the light source or dim or brighten the light source and to turn on or off the camera, take pictures, video, etc. The control system can also be configured to process images or video from the camera and display the video or pictures on the display, monitor, or screen.

In some embodiments as described above, the endoscope 114 comprises a working channel 114c configured to carry the optical fiber 108 and/or irrigation fluid (including the surfactant composition) through the length of the endoscope 114. In some embodiments, the optical fiber 108 and the irrigation fluid are carried through separate channels. However, for the purposes of FIG. 3A, the irrigation fluid and optical fiber 108 are carried through the same working channel 114c.

As indicated by the arrows egressing the working channel 114c, the irrigation fluid is configured to flow around the optical fiber 108 and out the end of the endoscope 114. Also, as shown, the optical fiber 108 is configured to terminate outside the end of the endoscope 112 and in the ureter of the subject or the subject's kidney K. It should be noted that the kidney stone 116 can be located in the kidney K, the ureter UR, or the bladder B of the subject S. As illustrated by the arrows emanating from the end of the optical fiber 108, the laser illustrated in FIG. 1 can transmit a laser light source to the kidney stone 116 via the optical fiber 108 and treat the kidney stone 116. Treating the kidney stone 116 can comprise breaking it up into smaller pieces to make it pass easier.

Figure 3B:
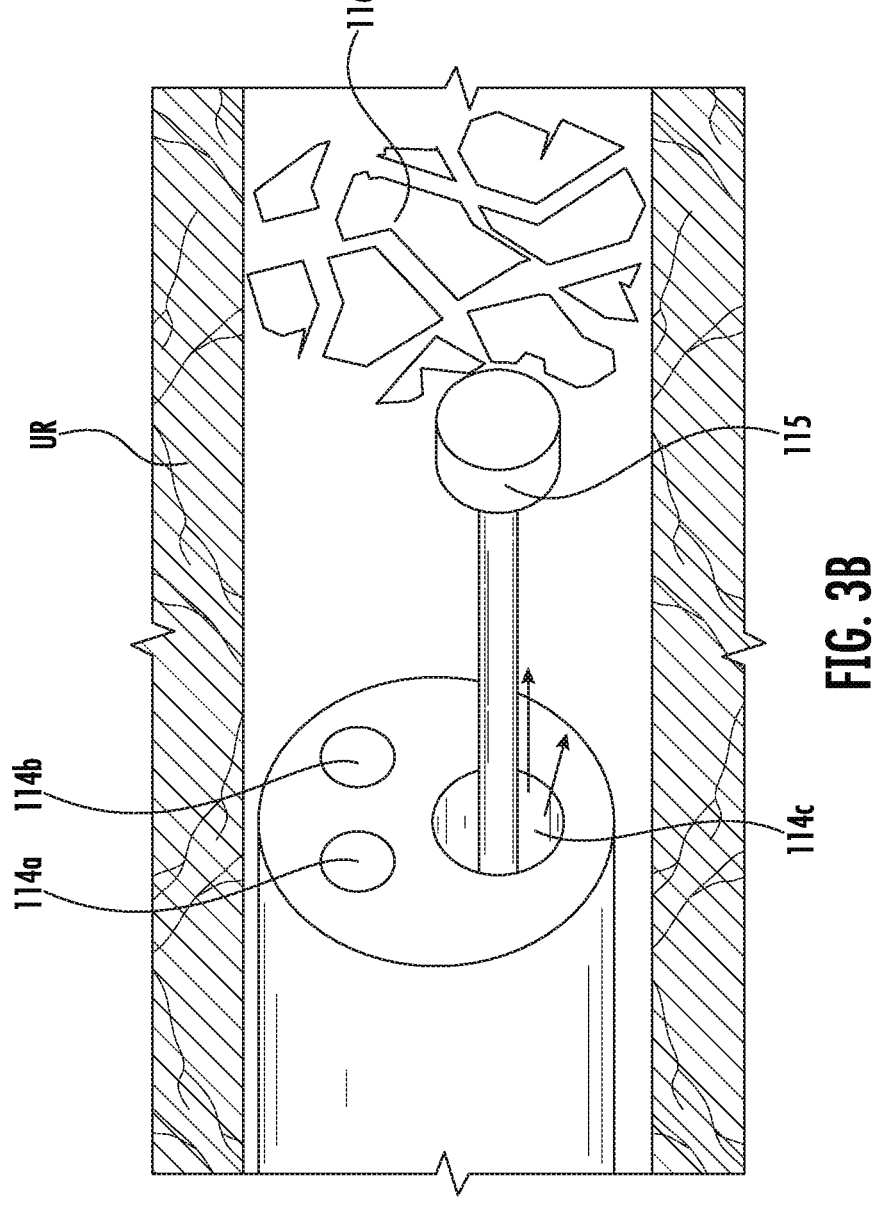

As illustrated in FIG. 3B, in some other embodiments, treating the kidney stone 116 can comprise breaking it up and removing it using a basket 115 configured for collecting one or more fragments of the kidney stone 116, the basket being controllably disposed in the working channel 114c of the endoscope 114. In such an embodiment, the control system described herein can be configured with a button, touchscreen, joy stick or other actuator configured to move the basket based on inputs from the medical professional or other user of the system 100. In other words, the user or medical professional can activate the button, touchscreen, joy stick, or other actuator on the control system and maneuver the basket to scoop, grab, etc. the kidney stone 116 or any fragment thereof. In some embodiments, instead of a basket, a claw, miniature crane, or other device can be controllable disposed in the working channel 114c of the endoscope 114 and be used for the same purpose (i.e., grabbing, scooping up, or otherwise obtaining the kidney stone 116).

While some embodiments of the present disclosure involve flowing an irrigation composition comprising a surfactant to the area in proximity to the location of the kidney stone 116, in some other embodiments, the subject matter herein involves flowing an irrigation composition free of the surfactant to the area in proximity to the location of the kidney stone or renal stone 116 after irradiating the kidney or renal stone 116 and/or the area in proximity to the location of the kidney stone 116. This is to help flush the kidney stone 116 from the kidney or other area.

Figure 4:
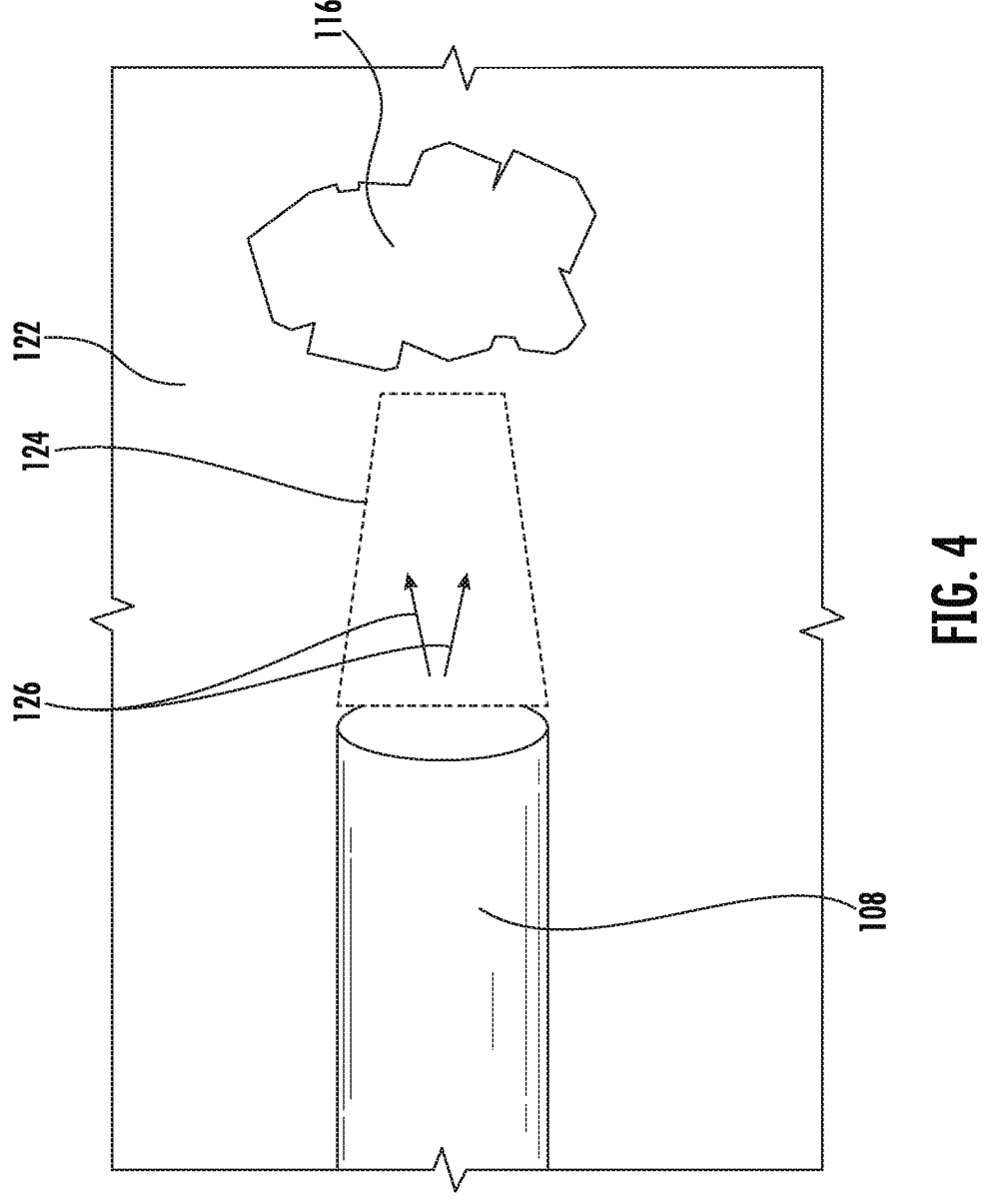
FIG. 4 illustrates another close-up view of the example laser lithotripsy system according to some embodiments of the present disclosure being used to perform kidney stone ablation and removal.

FIG. 4 illustrates another view of just the interaction between the optical fiber 104 and the kidney stone 116 in the context of an aqueous medium 122 (i.e., in the kidney or in the ureter of the subject S). As described above, when infrared (IR) lasers (e.g. Holmium and TFL) deliver energy, as illustrated by the arrows 126, through an optical fiber into a fluid environment (in this case, the urinary tract filled with fluid, augmented by the constant saline and surfactant irrigation through the working channel 114c of the ureteroscope 106 during the lithotripsy procedure), a vapor bubble 124 is created at the distal or delivery optical fiber tip 108. This laser-induced vapor bubble 124 results from the high-water absorption at these specific IR laser wavelengths. For the application of laser lithotripsy, the vapor bubble 124 produces both advantageous and disadvantageous effects. First, the vapor bubble 124 displaces the highly absorbing fluid, thus enabling a conduit for laser lithotripsy to be conducted in a non-contact mode with the optical fiber 108 tip to kidney stone distance in close proximity (on the order of a few millimeters). Second, the rapid expansion and contraction of the vapor bubble may produce significant pressure transients capable of removing stone material and providing a mechanical contribution to ablation, that enhances the otherwise primarily photothermal mechanism associated with long-pulse laser lithotripsy.

However, these pressure transients may also contribute to the undesirable phenomenon of stone "retropulsion" in which the stone is propelled backwards, away from the fiber tip, thus requiring the urologist to "chase after a moving target." The subject matter of the present disclosure includes using the surfactant composition in the irrigation fluid to help prevent retropulsion from occurring or at least reduce or minimize it. In some cases, larger bubbles allow longer non-contact working distances between the laser and the stone, which is advantageous in breaking down the stone. In some cases, collapse of larger bubbles may lead to more turbulence in the kidney during popcorning methods, which is also advantageous. In some embodiments, the surfactant in the surfactant composition is present at a concentration sufficient to enhance a length, width, and/or duration of the vapor bubble as compared to a vapor bubble generated in the absence of the surfactant composition.

As the irrigation fluid, including the surfactant composition, flows into the ureter and/or the kidney, the bubble 124 formed by the laser energy 126 from the optical fiber 108 is stronger and larger than a bubble formed in just the saline or other fluid in the ureter or kidney. The bubble can be evaluated using the techniques discussed elsewhere herein.

In some embodiments, the presently disclosed subject matter provides a kit. In some embodiments, the kit can be provided to a user for use in conjunction with a laser lithotripsy system as disclosed herein. For example, the kit can be provided to replace fluids, components, and the like once a user has consumed such materials that were initially provided with the system. In some embodiments, the kit comprises a reservoir as disclosed herein, wherein the reservoir comprising a surfactant composition as disclosed herein. For example, the kit can comprise an IV bag reservoir containing a composition comprising a surfactant. The composition can be a fluid or liquid, or can provided in power or dried form. In the case of a powdered or dried form, the kit can further comprise a liquid material for use in forming a solution or suspension of the surfactant for example. Thus, the kit can include instructions for implementing the reservoir in a laser lithotripsy system. Also, the reservoir can be configured for implementation in a laser lithotripsy system. In some embodiments, the kit can comprise a reservoir comprising an irrigation composition as described herein, where the irrigation composition is free of the surfactant.

In some embodiments, the kit can comprise a line for connecting the reservoir containing the surfactant composition to a working channel of an endoscope; and/or a line for connecting the reservoir containing the surfactant-free irrigation composition to a working channel of an endoscope. In some embodiments, the kit can comprise one or more valves configured for controlling flow from the line for connecting the reservoir comprising the surfactant composition to the working channel of the endoscope and from the line for connecting the reservoir containing the surfactant-free irrigation composition to the working channel of the endoscope. As mentioned above, the kit can include instructions for implementing the lines, reservoirs, and compositions in a laser lithotripsy system.

Figure 5:
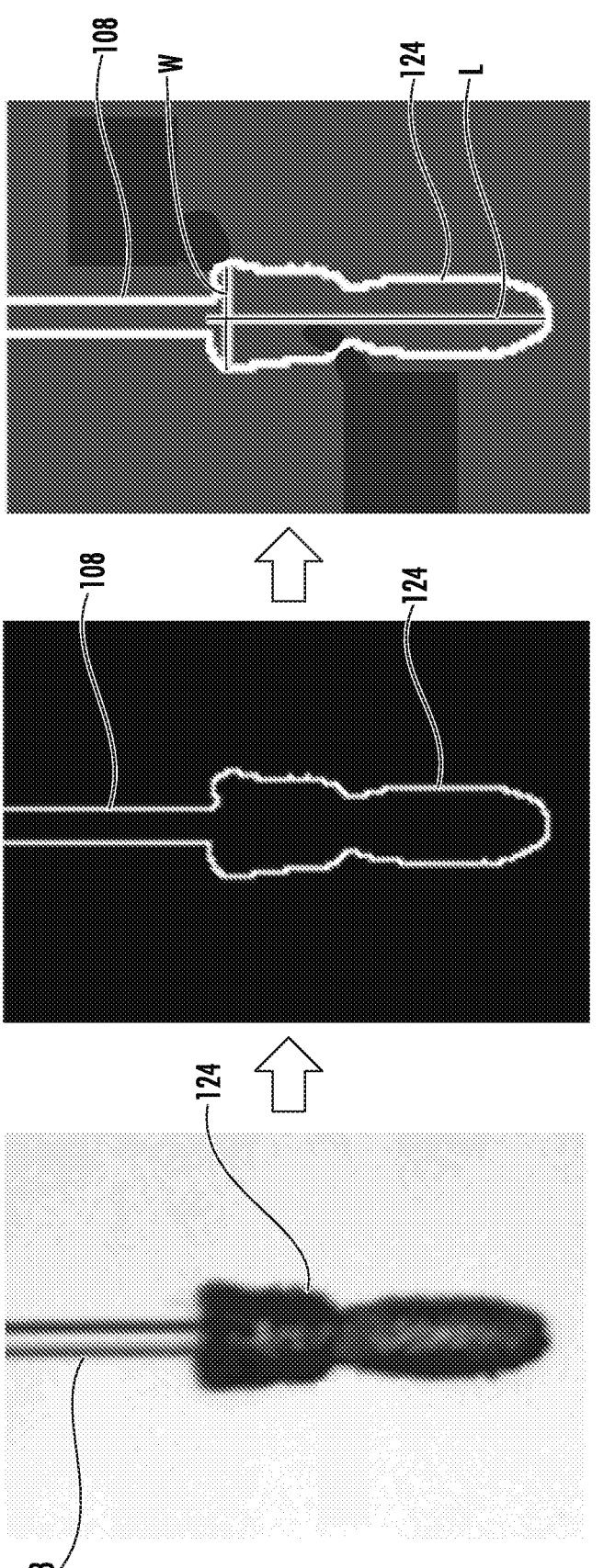
FIG. 5 includes several pictures and illustrations taken of a laser-induced vapor bubble formation, including a demonstration of measurement of the bubble size.

Experiments have been performed to generate the bubbles and determine their sizes. FIG. 5 includes several views of a picture of a laser-induced bubble formation 124 at the end of the optical fiber 108 and illustrates how their sizes were determined in the experiments. The far-left image is a picture taken of the bubble 124 and the middle and right pictures demonstrate how the sizes of the bubbles 124 can be measured using pixel size dimensions to determine their width and length. To approximate the size of the bubble 124 a binary analysis and computation of pixel size dimensions with conversion to micrometers can be performed. The bubble length L is defined as the distance from the distal or delivery fiber optic tip to the bottom of the bubble 124. The bubble width W is defined as the distance from one side of the bubble to the other side of the bubble measured in a direction perpendicular to the bubble length L and measured on the bubble 124 one pixel away from the distal or delivery fiber optic tip.

Figure 6:
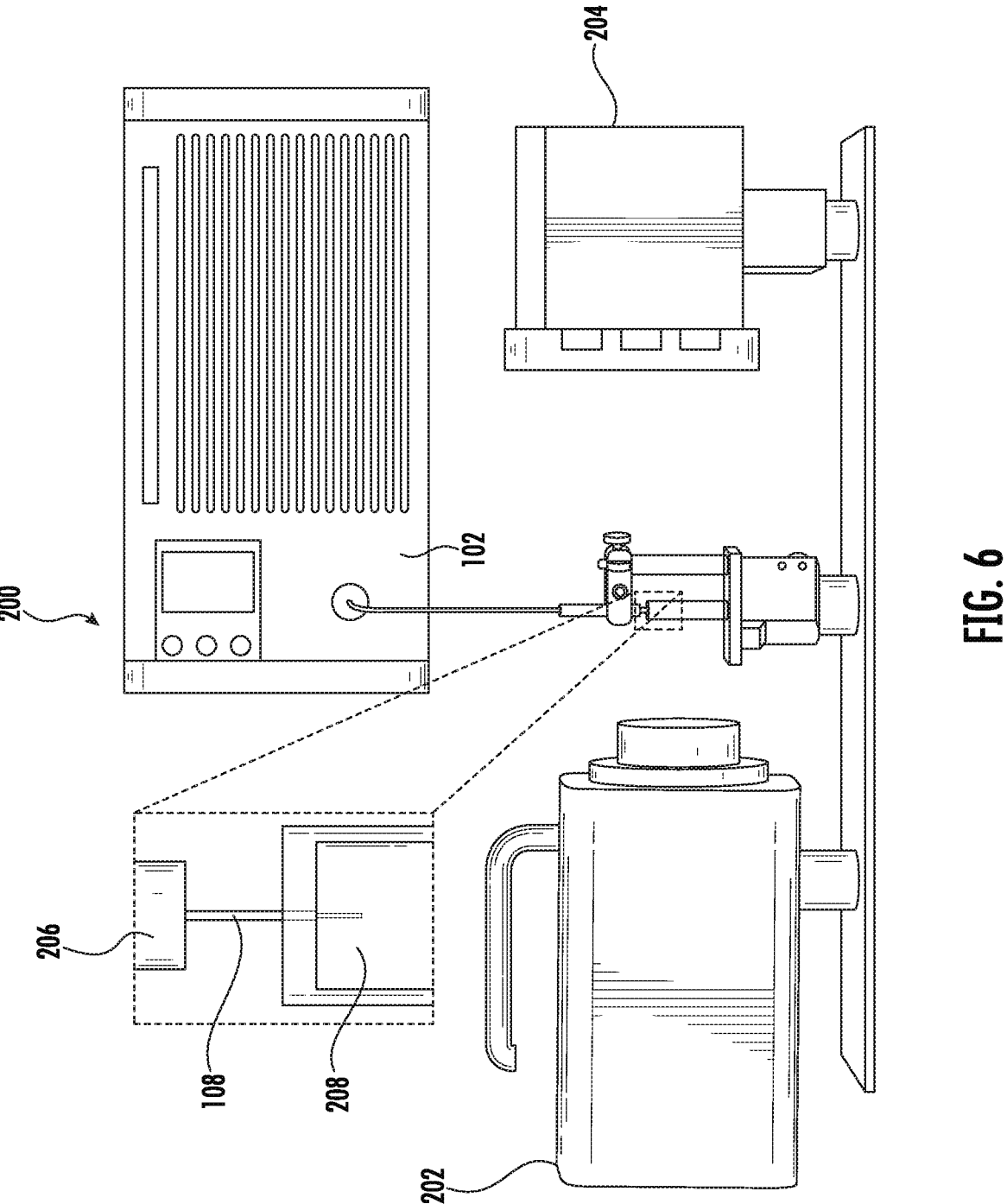
FIG. 6 illustrates an experimental setup for high-speed imaging of laser-induced vapor bubbles, including a magnified cutaway view of a fiber holder, fiber tip, and cuvette for holding fluid where the bubble is formed.

In order to set up this experiment, various components illustrated in FIG. 6 were used. The experimental setup 200 comprises a laser 102 providing a laser light source to the fiber optic 108 held in place by the fiber holder 206. The fiber optic 108 was inserted into a cuvette 208 with similar fluid similar to that found in the ureter or kidney along with that from the irrigation fluid and surfactant. The experimental setup 200 further comprises a camera 202 to capture images of the bubble(s) 124 and a lamp or (non-laser) light source for providing light to capture the picture.

During the experiment, the cuvette 208 holding the liquid was presented with laser energy from the laser 102 and one or more bubbles were formed in the liquid. The picture shown in FIG. 5 captured by a similar experimental setup can then be used to measure the size of the bubble 124.

This experimental setup compares differences in laser-induced bubble dynamics in surfactant solutions with varying concentrations and viscosity levels. A Thulium fiber laser 102 (IPG Medical, Marlborough, Mass., United States of America) was used with a center wavelength of 1940 nm and capable of operating at up to 500 W peak power, 50 W average power, and pulse rates up to 2000 Hz. The TFL was operated with pulse energies of 0.1 and 0.2 J, at pulse durations of 500 and 1000 μs, respectively. The laser energy was delivered through a standard 200-pm-core, low-OH, silica optical fiber 108 (BFL22-200, Thorlabs, Newton, N.J., United States of America), and numerical aperture (NA) of 0.22, with specifications similar to optical fibers currently used during clinical laser lithotripsy procedures. The TFL was externally modulated by a function generator to produce a single pulse. A high-speed camera (Nova S12, Photron, Tokyo, Japan) captured expansion and collapse of individual laser-induced vapor bubbles. The camera 202 was yoked to the laser trigger, enabling capture of a single laser pulse at 200,000 frames per second with resolution of 256×128 pixels. The optical fiber 108 was polished, clamped, and submerged into a 2.5 mL cuvette 208. A high-powered LED light source 204 (Zaila, Nila, Pasadena, Calif., United States of America) was used as a back light to provide contrast between the fiber optic tip suspended in the solution and the bubbles produced by a single laser pulse.

Polysorbate 80, polyoxyethylene sorbitan monooleate (Tween® 80 Biocompatible Surfactant, Cospheric LLC, Santa Barbara, Calif., United States of America) was used for enhancement of laser-induced vapor bubble dimensions during high-speed camera bubble imaging. Tween® 80 is a commonly used clinical surfactant agent and was chosen for this study due to its biocompatibility and potential as an irrigation substitute for laser lithotripsy. The agent was diluted with deionized water to concentrations ranging from 1-5%. To create a 1% concentration, 25 μL of Tween® 80 was syringed into 2.5 mL of deionized water and stirred until the agent was fully dissolved. To achieve higher concentrations, further 25 μL increments were added until the desired dilution was achieved. The study was performed first by recording a video of a single laser pulse in 2.5 mL of deionized water (0%, control). This procedure was repeated with 1-5% concentrations of Tween® 80, with a single sample size for each individual experimental group.

Bubble image data was then exported and analyzed in MATLAB (Version 2018b, MathWorks, Natick, Mass., United States of America). The MATLAB code mainly included edge detection image processing. The code first distinguished fiber edges from the background. It then detected edges of the forming bubble. The software tracked bubble expansion as it grew larger while still being attached to the fiber tip. The code was used to analyze bubble dimensions over time and identified the edge of bubble width and length. Since fiber dimensions were known, the distal or delivery fiber tip was used as a reference to convert pixel count into micrometers. The recorded maximum bubble values were documented under two conditions. First, the bubble had to remain open, providing a conduit. Second, the bubble had to stay connected to the fiber tip. No detached bubbles were recorded in this study.

The code also identified duration and number of bubble expansions and collapses during a single laser pulse. The formation of a "new bubble" was defined by where the previous bubble detached itself from the fiber optic tip (FIG. 7A through FIG. 7D below). After batch data was obtained, bubble formation frames were matched to the data to confirm validity of analysis code.

FIG. 7A through FIG. 7D illustrate several stages of one or more bubbles being formed over time while the laser 108 is energizing the liquid medium surrounding its distal or delivery end. FIG. 7A is a picture of a new bubble forming (i.e., just before it is formed). FIG. 7B is a picture of a bubble 124 that has expanded and continues to do so, expanding to full size. FIG. 7C is a picture of a bubble 124 detaching from the tip of the fiber optic 108 and formation of a new bubble. FIG. 7D is a picture of the new bubble 124 forming along with fragments of the old bubble 124 moving away from the tip of the fiber optic 108.

Table 1 summarizes all data from bubbles formed in 0-5% surfactant concentrations during a single laser pulse. No trends were found when looking at the percent difference of bubble dimensions between 1-5% concentrations. However, a difference was observed between the control study (0%) and studies using the most viscous solution at a 5% concentration.

TABLE 1

| LASER INDUCED VAPOR BUBBLE DIMENSIONS | | | | |
|---|---|---|---|---|
| Laser Settings | % Surfactant | # Bubbles | % larger Length | % larger Width |
| 500 μs | 0 | 3 | 0 (control) | 0 (control) |
| 0.1 J | 1 | 2 | 16.9 | 13.4 |
| | 2 | 2 | 31.3 | 35.8 |
| | 3 | 2 | 31.3 | 25.1 |
| | 4 | 2 | 19.3 | 22.8 |
| | 5 | 2 | 15.7 | 25.1 |
| 1000 μs | 0 | 6 | 0 (control) | 0 (control) |
| 0.2 J | 1 | 4 | 19.7 | 16.2 |
| | 2 | 4 | 23.6 | 38.6 |
| | 3 | 4 | 35.9 | 25.6 |
| | 4 | 4 | 18.6 | 25.6 |
| | 5 | 4 | 23.0 | 29.9 |

During IR laser lithotripsy, laser energy exiting from the fiber tip in a fluid medium is strongly absorbed by the water, resulting in vaporization of the water and creation of a vapor bubble. This laser-induced vapor bubble rapidly expands, providing a conduit for laser energy to reach the kidney stone in non-contact mode. The vapor bubble also produces strong pressure transients that can provide a mechanical contribution to stone ablation as well as stone movement, commonly referred to as stone retropulsion. Manipulation of laser-induced vapor bubble dimensions may potentially contribute to (1) stone ablation at longer non-contact working distances, (2) use of lower laser pulse energies resulting in more efficient stone ablation, and (3) stronger fluid turbulence in the kidney calyces for greater stone movement and improved stone ablation during "popcorn" mode of laser lithotripsy. The presently disclosed subject matter demonstrates that viscous solutions utilizing a biocompatible and commercial surfactant create larger and longer lasting vapor bubbles during IR irradiation with a Thulium fiber laser.

The underlying basic principle for bubble formation involves the pressure differential between the inside, the outside, and the surface tension of the bubble. Bubbles formed in purely water are unstable due to the high surface tension, (72 dynes/cm), which cause them to quickly collapse. When surfactant is integrated into water at particular concentrations, the surface tension is lowered and bubbles become more stable. In order for the bubble to be more stable, the pressure of the gas vapor inside the bubble, $P_{in}$, needs to be larger than the outside bubble pressure plus the pressure created by surface tension, as shown in equation 1 [23].

$$P_{in} = P_{out} + \frac{2s}{r} \qquad (1)$$

$P_{out}$ is all of the atmospheric pressure and water pressure pushing inward on the newly forming bubble, s is the surface tension of the solution the bubble is forming in, and r is the radius of the bubble. When Tween® 80 is added to water at a concentration of 1%, the surface tension is lowered to about 38 dynes/cm [24]. With lower surface tension, formation of longer lasting, larger, and fewer bubbles are expected.

As observed in Table 1, the lengths and widths of the bubbles formed are on average about 25% larger when produced inside viscous solutions, with all concentrations greater than 1%. This 25% increase in bubble dimensions while attached to the fiber tip translates into a longer conduit which allows laser energy to travel further in the solution without absorption. Table 1 also shows that during a single laser pulse, fewer bubbles are formed in concentrations larger than 1%. Fewer bubbles connected to the fiber tip for a longer duration also create a temporally extended conduit allowing higher energy to propagate without absorption by the solution.

In a second test implementation, the results of which are shown in Table 2 below, a Thulium fiber laser (TLR-50/500, IPG Medical, Marlborough, Mass., United States of America) was used with a center wavelength of 1940 nm. The TFL was operated with pulse energies of 0.05, 0.1, 0.2, and 0.5 J, and pulse durations of 250, 500, 1000, and 2500 μs, providing a constant peak power of 200 W for each set of data. Laser energy was delivered through a 200-μm-core, low-OH, silica optical fiber (BFL22-200, Thorlabs, Newton, N.J., United States of America), with numerical aperture, NA=0.22 (similar to clinical optical fibers used in lithotripsy). The TFL was modulated by a function generator (DS345, Stanford Research Systems, Sunnyvale, Calif., United States of America) to produce a single pulse. A temporal beam profile providing the energy distribution during a single laser pulse was acquired using a photovoltaic infrared photodetector (PD-10.6, Boston Electronics, Brookline, Mass., United States of America) to confirm laser stability. For simplicity and clarity in the graphs, the laser temporal beam profile data was smoothed by a standard Gaussian filter with 10 μs width using MATLAB (Version 2018b, MathWorks, Natick, Mass., United States of America).

A high-speed camera (Nova S12, Photron, Tokyo, Japan) captured the vapor bubble dynamics. The camera was linked to the laser trigger, enabling capture of a single laser pulse at 200,000 frames per second with a resolution of 256×128 pixels. The optical fiber was polished, clamped, and then submerged into a 4.5 mL transparent cuvette. A high-power, light-emitting diode (LED) source (Zaila, Nila, Pasadena, Calif., United States of America) coupled with an optical diffuser was used as a back light to provide contrast between the fiber optic tip suspended in the solution and the bubbles produced by a single laser pulse.

Polysorbate 80, polyoxyethylene sorbitan monooleate (Tween®80 Biocompatible Surfactant, Cospheric, Santa Barbara, Calif., United States of America) was used as the surfactant for all experiments for Table 2. The agent was diluted in deionized water to concentrations up to 10%. These concentrations only affected the physical properties of the fluid, but not its physical appearance, which allowed the solution to remain visibly clear.

Figures 8A, 8B, 8C:
FIG. 8A through FIG. 8C includes photographs of laser-induced vapor bubbles (2500 microseconds and 0.5 J laser energy) at peak length dimensions.

FIG. 8A is a photograph of a bubble 124 being formed in water, which was the control. FIG. 8B is a photograph of a bubble 124 being formed in a 5% by weight concentration of surfactant. FIG. 8C is a photograph of a bubble 124 being formed in a 10% by weight concentration of surfactant. As illustrated by the pictures, a higher concentration of surfactant can increase the size of the bubble 124 formed. This can be very useful when dealing with kidney stones that are further away or otherwise in general to make the reach of the laser energy further.

Figure 9:
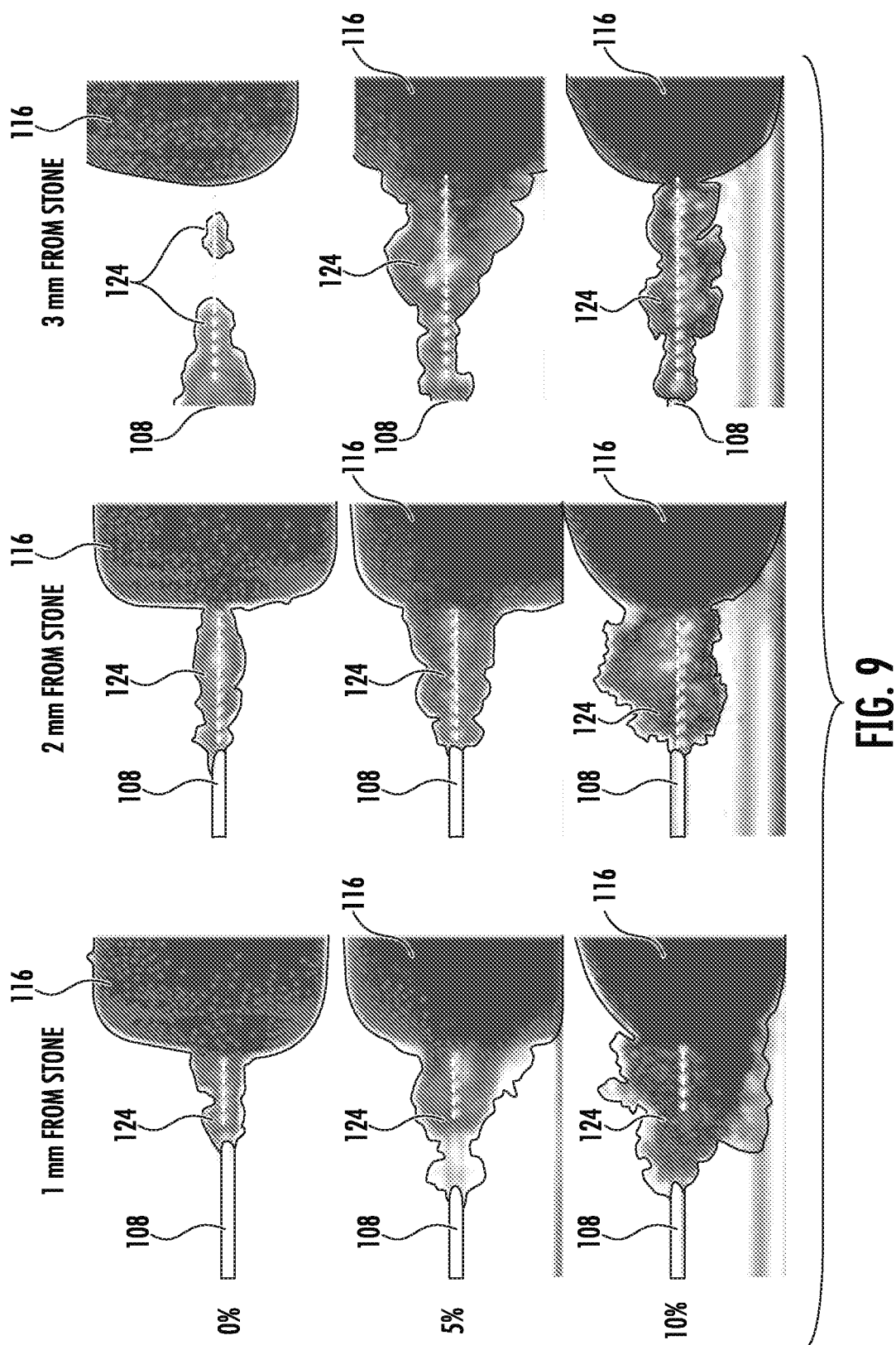
FIG. 9 includes photographs of laser-induced vapor bubbles near a calcium oxalate monohydrate (COM) kidney stone, at various working distances from the fiber optic tip, including 1, 2, and 3 mm.

FIG. 9 includes photographs of bubbles 124 being formed next to a COM kidney stone 116 at various distances (i.e., 1-3 mm away). Additionally, as the photographs go from top to bottom, the concentration (by weight) of surfactant that is included in the irrigation fluid is increased (i.e., from 0% to 10%). As illustrated in the photographs, a higher concen-

TABLE 2

LASER INDUCED VAPOR BUBBLE DIMENSIONS

| Laser Settings | Concentration (%) | Number of Bubbles | Length (μm) | Width (μm) | Duration (μs) |
|---|---|---|---|---|---|
| 250 μs | 0 | 2 ± 0.0 | 2585 ± 131 | 1368 ± 77 | 126 ± 46 |
| 0.05 J | 5 | 1 ± 0.0 | 3198 ± 46* | 1790 ± 28* | 214 ± 5* |
| | 10 | 1 ± 0.0 | 2585 ± 29 | 1530 ± 17* | 230 ± 11* |
| 500 μs | 0 | 4 ± 0.0 | 2318 ± 83 | 1241 ± 60 | 127 ± 38 |
| 0.1 J | 5 | 2.5 ± 0.8 | 2875 ± 285* | 1437 ± 135 | 239 ± 61* |
| | 10 | 1 ± 0.0 | 2695 ± 62* | 1464 ± 25* | 532 ± 13* |
| 1000 μs | 0 | 6.5 ± 0.5 | 2350 ± 185 | 1319 ± 85 | 151 ± 19 |
| 0.2 J | 5 | 5 ± 0.5 | 2733 ± 225* | 1588 ± 220 | 217 ± 99 |
| | 10 | 3.3 ± 0.4 | 3028 ± 315* | 1473 ± 58* | 309 ± 90* |
| 2500 μs | 0 | 13.3 ± 3.0 | 2430 ± 91 | 1311 ± 76 | 186 ± 114 |
| 0.5 J | 5 | 6.5 ± 1.7 | 3743 ± 405* | 1563 ± 89* | 352 ± 177 |
| | 10 | 5.3 ± 1.6 | 4185 ± 535* | 1411 ± 18 | 528 ± 423 |

Table 2 summarizes the data (length, width, and duration) from bubbles formed at 0, 5, and 10% surfactant concentrations (n=4). For each individual set of laser parameters (pulse duration in microseconds and pulse energy in Joules) and surfactant concentration (%), the bubble dimensions and lifetime were recorded (average ±standard deviation) and observed to be relatively consistent. Table 2 also shows the total number of bubbles formed during a single laser pulse. As an example, for the specific laser parameters of 500 ps and 0.1 J, when observing both bubble length and width, there are an average of four peaks when laser irradiation occurs in water, compared with an average of 2.5 peaks for a 5% surfactant concentration, and only one peak for a 10% concentration. This trend of fewer bubble formations for 5% and 10% concentrations is also observed within all of the other sets of laser parameters as well (250 μs at 0.05 J, 1000 μs at 0.2 J, and 2500 μs at 0.5 J). Fewer bubbles formed in viscous solutions for all concentrations tested (5% and 10%), compared to water (0%). Bubbles formed in 5% solution were about 29% longer, 22% wider and 72% longer lasting, while bubbles formed in 10% solution were 29% longer, 12% wider and 169% longer lasting than bubbles formed in water (Table 2). The asterisks in the individual data sets denote a statistically significant result (p<0.05) between the individual bubble characteristics (length, width, or duration) for 5% and 10% surfactant concentrations versus the control study (water, 0%). Table 2 also shows that, during a single laser pulse, fewer bubbles are formed for higher surfactant concentrations.

FIG. 8A through FIG. 8C include photographs of laser-induced vapor bubbles generated by lasers (2500 μs and 0.5 J) at peak length dimensions.

tration of surfactant makes for larger bubbles 124 that hold up between the optical fiber 108 and the kidney stone 116.

Figure 10A:
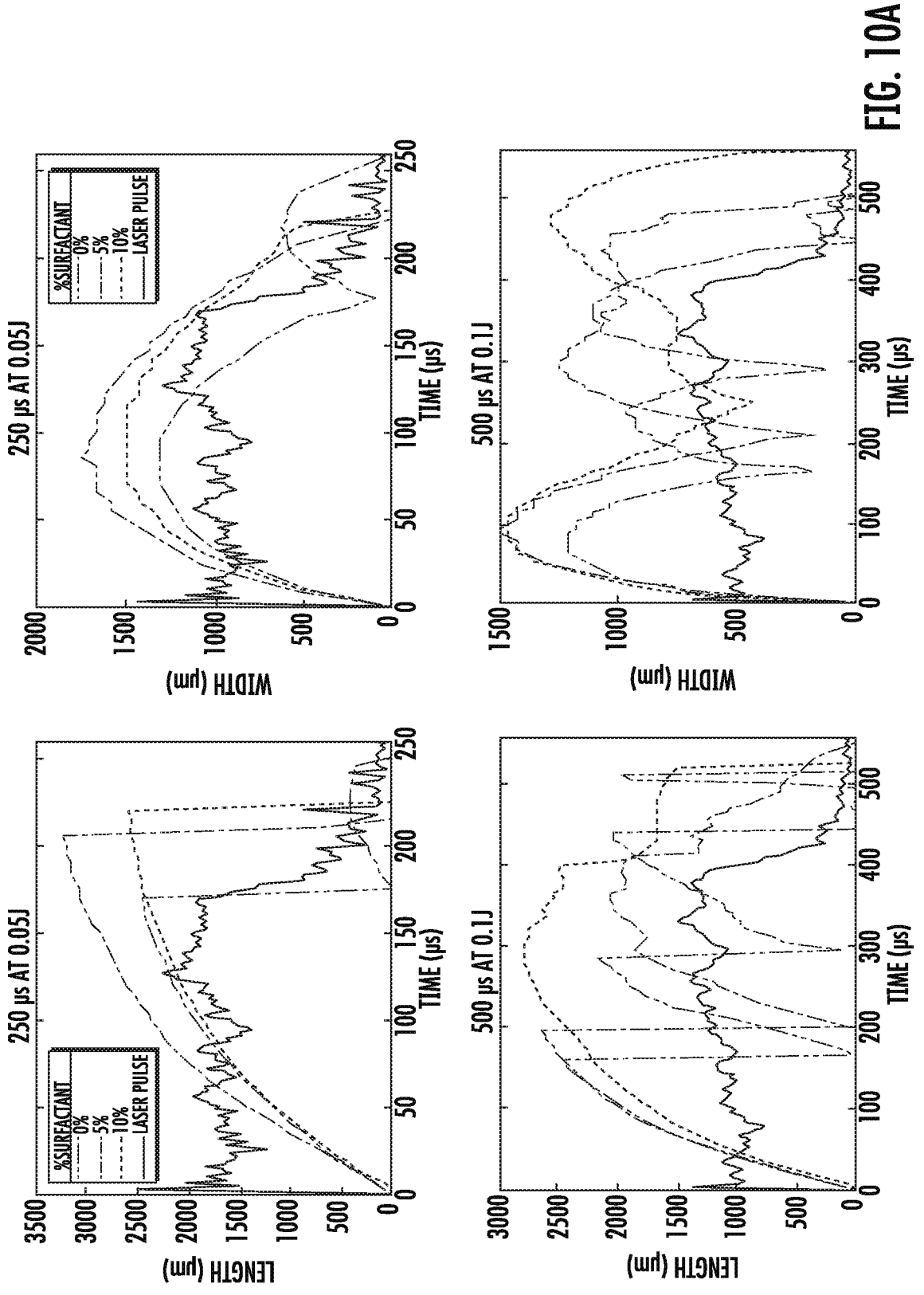
FIG. 10A through FIG. 10B includes several charts illustrating TFL-induced vapor bubble dimensions while bubbles remained attached to the fiber tip, as a function of time and surfactant concentration, super imposed with average laser pulse profile; the legend shown in the top charts in FIG. 10A should be used for all of the charts in FIG. 10A and FIG. 10B.
Figure 10B:
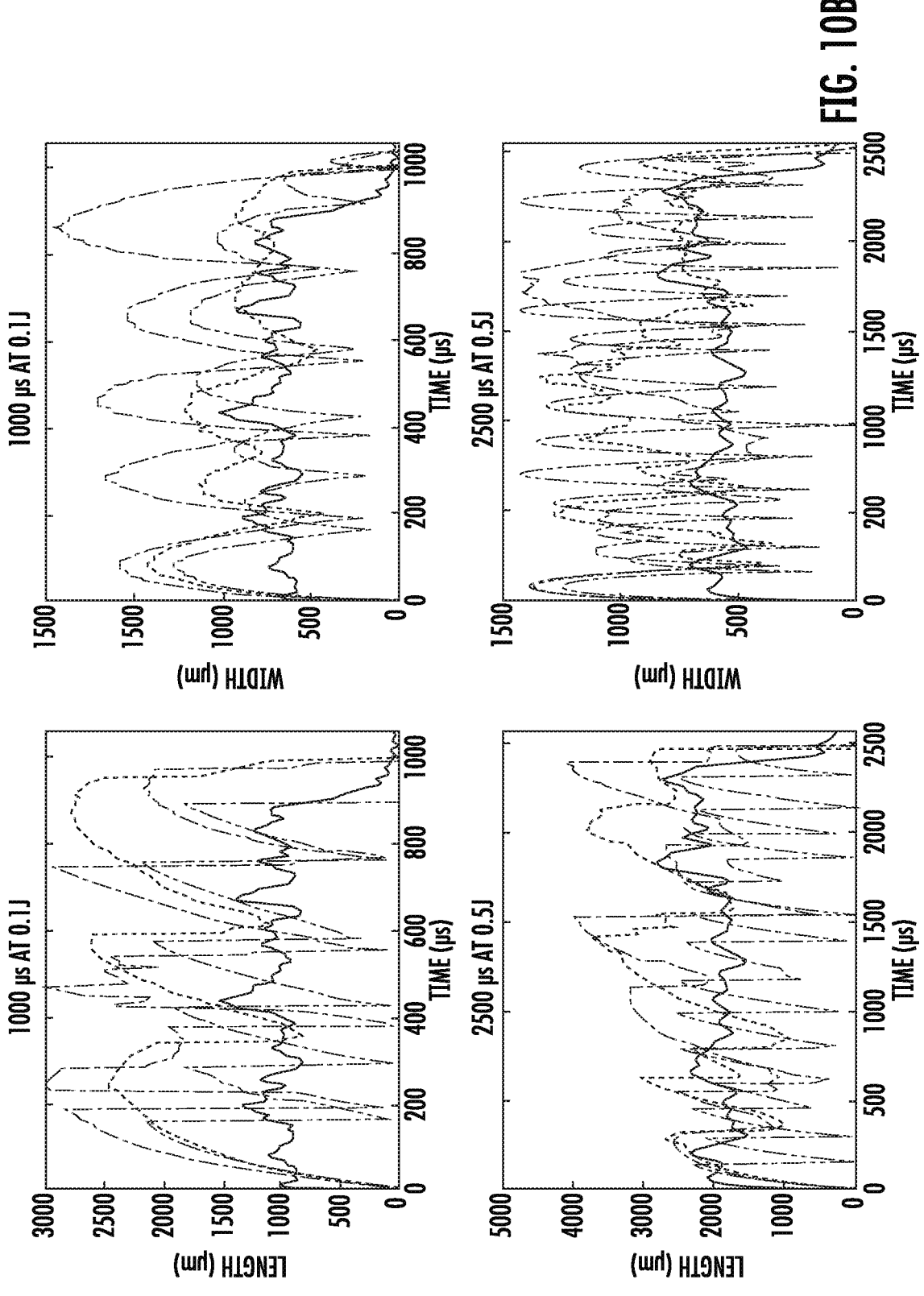

FIG. 10A and FIG. 10B displays the TFL temporal beam profile (solid line) and bubble lifetime and dimensions while in contact with the fiber tip, using laser pulse energies of 0.05 J, 0.1 J, and 0.5 J and pulse durations of 250, 500, 1000, and 2500 ps, for 0%, 5%, and 10% concentrations. These figures illustrate the width and length of TFL-induced vapor bubbles, while the bubbles remained attached to the fiber optic tip, as a function of both time and surfactant concentration, superimposed with the laser pulse profile (solid line) for the parameters described.

As the laser pulse begins, the bubble starts to expand, and as laser pulse continues, the bubble continues its expansion until it detaches from the fiber. At this time point, a second bubble forms and the original bubble begins to collapse. As the laser pulse ends, the bubble stops expanding and collapses. The 5% and 10% concentrations increased vapor bubble width, length, and lifetime versus the control study (0%) without surfactant. Bubble expansion occurred at similar rates, however, the bubble forming in viscous solution lasted longer, which in turn created a larger bubble.

FIG. 11 is a flow chart illustrating an example method 1100 according to some embodiments of the present disclosure. In some embodiments, the first step 1102 in the method 1100 comprises inserting a ureteroscope into a subject to an area in proximity to a location of the renal stone, wherein the ureteroscope comprises an endoscope comprising an optical fiber and a working channel. In some embodiments, the second step 1104 in the method 1100 comprises flowing a surfactant composition through the working channel in the endoscope to the area in proximity to the location of the kidney stone. In some embodiments, an optional third step 1106 in the method 1100 comprises irradiating the renal stone and/or the area in proximity to the location of the renal stone with a laser using the optical fiber in the ureteroscope, to thereby treat the renal stone in the subject. In some embodiments, an optional fourth step 1108 in the method 1100 comprises flowing an irrigation composition free of the surfactant to the area in proximity to the location of the renal stone after irradiating the renal stone and/or the area in proximity to the location of the renal stone. In some embodiments, the third step 1106 generates one or more fragments of the renal stone and the method 1100 comprises collecting the one or more fragments using a basket, claw, grabber, crane, or other suitable acquisition tool.

The presently disclosed subject matter is not limited to infrared laser systems or medical applications. Rather, it can be implemented in any system where a fluid medium exists in a space between the delivery device and the target and wherein the fluid medium absorbs the laser wavelength. The target can be any tissue in a subject, including any tissue that might be treated by laser ablation. For example, the presently disclosed subject matter can be used with a carbon dioxide laser for treating tissues immersed in water. It should also be understood that the presently disclosed subject matter has utility in situations where the absorption of the liquid medium is not based on the primary liquid molecules but on particulates dissolved in the liquid. For example, proteins dissolved in water or blood are highly absorptive of ultraviolet radiation.

The present subject matter can be embodied in other forms without departure from the spirit and essential characteristics thereof. The embodiments described therefore are to be considered in all respects as illustrative and not restrictive. Although the present subject matter has been described in terms of certain specific embodiments, other embodiments that are apparent to those of ordinary skill in the art are also within the scope of the present subject matter.

REFERENCES

Each of the following references is expressly incorporated by reference herein in their entireties.

[1] T. Vos, et al, "Global, regional, and national incidence, prevalence, and years lived with disability for 301 acute and chronic diseases and injuries in 188 countries, 1990-2013: a systematic analysis for the Global Burden of Disease Study 2013," *Lancet,* vol. 386, no. 9995, pp. 743-800, 2015.

[2] D. Bagley and M. Erhard, "Use of the holmium laser in the upper urinary tract," *Tech. Urol.,* vol. 1, no. 1, pp. 25-30, 1995.

[3] N. M. Fried and P. B. Irby, "Advances in laser technology and fiber optic delivery systems for use in lithotripsy," *Nat. Rev. Urol., vol.* 15, no. 9, pp. 563-573, 2018.

[4] N. M. Fried, "Recent advances in infrared laser lithotripsy," Biomed. *Opt. Express, vol.* 9, no. 9, pp. 4552-4568, 2018.

[5] A. G. Martov, D. V. Ergakov, M. A. Guseinov, A. S. Andronov, S. V. Dutov, V. A. Vinnichenko, and A. A. Kovalenko, "Initial experience in clinical application of thulium laser contact lithotripsy for transurethral treatment of urolithiasis," *Urologiia,* March, no. 1, 2018.

[6] O. Traxer, "Thulium fiber laser: the new player for kidney stone treatment? A comparison with Holmium: YAG laser," *World J. Urol.,* 2019.

[7] P. Kronenberg and 0. Traxer, "The laser of the future: reality and expectations about the new thulium fiber laser—a systematic review," *Transl. Androl. Urol., vol.* 8, suppl. 4, 2019.

[8] L. A. Hardy, P. B. Irby, and N. M. Fried, "Scanning electron microscopy of real and artificial kidney stones before and after Thulium fiber laser ablation in air and water," *Proc. SPIE,* vol. 104680G, pp. 1-11, 2018.

[9] K. F. Chan, G. J. Vassar, T. J. Pfefer, J. M. Teichman, R. D. Glickman, S. T. Weintraub, and A. J. Welch, "Holmium:YAG laser lithotripsy: a dominant photothermal ablative mechanism with chemical decomposition of urinary calculi," *Lasers Surg. Med.,* vol. 25, no. 1, pp. 22-37, 1999.

[10] K. F. Chan, T. J. Pfefer, J. M. H Teichman, and A. J. Welch, "A perspective on laser lithoripsy: the fragmentation process," *J. Endourol,* vol. 15, no. 3, pp. 257-273, 2001.

[11] H. Loertscher, W. Shi, and W. Grundfest, "Tissue ablation through water with Erbium:YAG lasers," *IEEE Trans. Biomed. Eng.,* vol. 39, no. 1, pp. 86-88, 1992.

[12] T. Asshauer, K. Rink, and G. Delacretaz, "Acoustic transient generation by holmium-laser-induced cavitation bubbles," *J. Appl. Phys.,* vol. 76, no. 9, pp. 5007-5013, 1994.

[13] M. Frenz, H. Pratisto, F. Konz, E. D. Jansen, A. J. Welch, and H. P.

Weber, "Comparison of the effects of absorption coefficient and pulse duration of 2.12-□m and 2.79-□m radiation on laser ablation of tissue," *IEEE J. Sel. Top. Quantum Electron.,* vol. 32, no. 12, pp. 2025-2035, 1996.

[14] H. Pratisto, M. Frenz, M. Ith, H. J. Altermatt, E. D. Jansen, and H. P.

Weber, "Combination of fiber-guided pulsed erbium and holmium laser radiation for tissue ablation under water," *Appl. Opt.,* vol. 35, no. 19, pp. 3328-3337, 1996.

[15] E. D. Jansen, T. Asshauer, M. Frenz, M. Motamedi, G. Delacretaz, and A. J. Welch, "Effect of pulse duration on bubble formation and laser-induced pressure waves during holmium laser ablation," *Lasers Surg. Med.,* vol. 18, no. 3, pp. 278-293, 1996.

[16] M. Frenz, F. Konz, H. Pratisto, H. P. Weber, A. S. Silenok, and V. I. Konov, "Starting mechanisms and dynamics of bubble formation induced by a Ho:Yttrium aluminum garnet laser in water," *J. Appl. Phys.,* vol. 84, no. 11, pp. 5905-5912, 1998.

[17] O. Fohn, H. S. Pratisto, F. Konz, M. Ith, J. Altermatt, M. Frenz, and H. P. Weber, "Side-firing fiber device for underwater tissue ablation with Ho:YAG and Er:YAG laser radiation," *J. Biomed. Opt.,* vol. 3, no. 1, pp. 112-122, 1998.

[18] P. Zhong, H. L. Tong, F. H. Cocks, M. S. Pearle, and G. M. Preminger, "Transient cavitation and acoustic emission produced by different laser lithotripters," *J. Endourol.,* vol. 12, no. 4, pp. 371-374, 1998.

[19] J. W. Dushinski and J. E. Lingeman, "High-speed photographic evaluation of holmium laser," *J. Endourol.,* vol. 12, no. 2, pp. 177-181, 1998.

[20] A. Vogel and V. Venugopalan, "Mechanisms of pulsed laser ablation of biological tissues," *Chem. Rev.,* vol. 103, no. 2, pp. 577-644, 2003.

[21] T. Lu, Q. Xiao, D Xia, K. Ruan, and Z. Li, "Cavitation effect of holmium laser pulse applied to ablation of hard tissue underwater," *J. Biomed. Opt.,* vol. 15, no. 4, pp. 048002, 2010.

[22] L. A. Hardy, J. D. Kennedy, C. R. Wilson, P. B. Irby, and N. M. Fried, "Analysis of Thulium fiber laser induced vapor bubbles for ablation of kidney stones," *J. Biophotonics,* vol. 10, no. 10, pp. 1240-1249, 2017.

[23] D. B. Robert "The Formation of Bubbles," *J. Applied Physics,* vol. 15, no. 5, pp. 446-451, 1943.

[24] S. C. Kothekar, A. M. Ware, J. T. Waghmare, and S. A. Momin, "Comparative analysis of the properties of Tween-20, Tween-60, Tween-80, Arlacel-60, and Arlacel-80," *J. Dispersion Science and Technology,* vol. 28, no. 3, pp. 477-484, 2007.

[25] Y. A. Pishchalnikov, W. Behnke-Parks, K. Maeda, T. Colonius, M. Mellema, M. Hoperoft, A. Luong, S. Wiener, M. L. Stoller, and D. J. Laser, "Experimental observations and numerical modeling of lipid-shell microbubbles with calcium-adhering moieties for minimally-invasive treatment of urinary stones," *Proc. Mtgs. Acoust.,* vol. 35, pp. 020008, 2018.

[26] K. R. Ghani, A. H. Aldoukhi, K. M. Black, W. W. Roberts, W. Behnke-Parks, and M. Stoller, "Augmentation of non-contact holmium laser lithotripsy with targeting microbubbles," *Photonics West,* Abstract #10852-21, Feb. 2, 2019.

[27] M. Stoller, "Tagged microbubbles: a potential new minimally invasive technique for urinary stone disease," Stonelab Symposium, AUA Headquarters, Linthicum, Md., Dec. 6-7, 2019.

[28] U.S. Pat. No. 5,321,715 to Trost.

What is claimed is:

1. A method of irradiating a target with laser radiation; by an optical fiber having a delivery end, the method comprising:

spacing the delivery end of the optical fiber from a target end of the optical fiber by a space;

occupying the space between the delivery end of the optical fiber and the target end of the optical fiber with a liquid medium;

administering a surfactant composition to the liquid medium;

generating a first laser pulse, wherein the first laser pulse has a wavelength and sufficient energy to form a vapor bubble in the liquid medium at the delivery end of the optical fiber;

delivering the first laser pulse from the delivery end of the optical fiber to the liquid medium, wherein the liquid medium absorbs the wavelength, and the energy forms the vapor bubble, wherein the vapor bubble includes a surfactant of the surfactant composition; and allowing the vapor bubble to expand an amount sufficient to displace a portion of the liquid medium from the space between the delivery end of the optical fiber and the target.

2. The method of claim 1, further comprising generating one or more additional laser pulses, wherein the one or more additional laser pulses are delivered to the target through the vapor bubble.

3. The method of claim 1, wherein the surfactant composition comprises; a surfactant at a concentration of about 0.1% to about 10% by weight of total composition; and a carrier suitable for administration in the liquid medium.

4. The method of claim 3, wherein the surfactant is present at a concentration ranging from about 1% to about 2% by weight of total composition.

5. The method of claim 3, wherein the carrier comprises a component selected from the group consisting of water, a buffer, an electrolyte, a solution suitable for intravenous administration in a subject, and a solution isotonic to the liquid medium.

6. The method of claim 5, wherein the electrolyte is selected from the group consisting of sodium, chlorine, potassium, and combinations thereof.

7. The method of claim 5, wherein the electrolyte is present as sodium chloride at a concentration of about 0.3% to about 1.2% by weight of total solution.

8. The method of claim 1, wherein the surfactant is selected from the group consisting of an anionic surfactant, a nonionic surfactant, a cationic surfactant, and a zwitterionic surfactant.

9. The method of claim 8, wherein the nonionic surfactant is a polysorbate surfactant.

10. The method of claim 9, wherein the polysorbate surfactant is selected from the group consisting of polysorbate 20, polysorbate 60, and polysorbate 80.

11. The method of claim 1, wherein the wavelength of the laser pulse comprises an infrared wavelength, optionally wherein the infrared wavelength ranges from about 1450 nm to about 2200 nm.

12. The method of claim 1, wherein the laser is selected from the group consisting of an indium phosphide diode laser, a thulium fiber laser (TFL), a thulium: YAG solid-state laser, and a holmium: YAG solid-state laser.

13. The method of claim 1, wherein the laser comprises one or more parameters selected from the group consisting of:

a pulse energy ranging from about 0.025 to about 6.0 Joules;

a pulse duration ranging from about 200 to about 20,000 microseconds;

a pulse repetition rate ranging from about 5 to about 2,000 Hertz; and an average power ranging from about 1 to about 200 watts.

14. The method of claim 1, wherein the target is located in an area internal to a subject and the liquid medium is present in the area internal to the subject.

15. The method of claim 14, wherein the target is a tissue or other structure in the subject.

16. The method of claim 15, wherein the other structure is a urinary tract stone, a gastrointestinal stone, or a salivary stone.

* * * * *